United States Patent
Yu et al.

(10) Patent No.: US 10,702,552 B2
(45) Date of Patent: Jul. 7, 2020

(54) SIRNA OF HUMAN IL-6 AND RECOMBINANT EXPRESSION CAR-T VECTOR AND THEIR CONSTRUCTION METHODS AND APPLICATIONS

(71) Applicant: SHANGHAI UNICAR-THERAPY BIO-MEDICINE TECHNOLOGY CO., LTD, Shanghai (CN)

(72) Inventors: Lei Yu, Shanghai (CN); Liqing Kang, Shanghai (CN); Zhou Yu, Shanghai (CN)

(73) Assignee: SHANGHAI UNICAR-THERAPY BIO-MEDICINE TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 16/331,142

(22) PCT Filed: Nov. 10, 2016

(86) PCT No.: PCT/CN2016/105263
§ 371 (c)(1),
(2) Date: Mar. 7, 2019

(87) PCT Pub. No.: WO2018/068354
PCT Pub. Date: Apr. 19, 2018

(65) Prior Publication Data
US 2019/0201445 A1    Jul. 4, 2019

(30) Foreign Application Priority Data

Oct. 11, 2016  (CN) .......................... 2016 1 0887703

(51) Int. Cl.
| | | |
|---|---|---|
| A61K 35/17 | (2015.01) | |
| A61K 39/00 | (2006.01) | |
| A61K 31/713 | (2006.01) | |
| C12N 15/113 | (2010.01) | |
| A61P 35/02 | (2006.01) | |
| C12N 15/85 | (2006.01) | |
| C12N 15/86 | (2006.01) | |
| C12N 5/0783 | (2010.01) | |
| C12N 15/66 | (2006.01) | |

(52) U.S. Cl.
CPC .............. *A61K 35/17* (2013.01); *A61P 35/02* (2018.01); *C12N 5/0636* (2013.01); *C12N 15/1136* (2013.01); *C12N 15/66* (2013.01); *C12N 15/85* (2013.01); *C12N 15/86* (2013.01); *C12N 2310/14* (2013.01); *C12N 2510/00* (2013.01); *C12N 2740/15043* (2013.01)

(58) Field of Classification Search
None
See application file for complete search history.

(56) References Cited

FOREIGN PATENT DOCUMENTS

WO    2014011984 A1    1/2014

OTHER PUBLICATIONS

Burnet FM, Immunological aspects of malignant disease, Lancet, Jun. 3, 1967.
Sharp, RNA Interference-2001, Genes & Dev., 2001, 15:485.
Emily Bernstein, Role for a bidentate ribonuclease in the initiation step of RNA interference, NATURE, Jan. 18, 2001, vol. 409.
Antti Nykanen, ATP Requirements and Small Interfering RNA Structure in the RNA Interference Pathway, CELL, Nov. 2, 2001, vol. 107, pp. 309-321.
Sayda M. Elbashir, RNA interference is mediated by 21- and 22-nucleotide RNAs, Genes & Dev., 2001, 15:188.
Kisielow M., Isoform-specific knockdown and expression of adaptor protein ShcA using small interfering RNA, Journal of Biochem., 2002, 363, 1-5.
Porter DL, Chimeric Antigen Receptor-Modified T Cells in Chronic Lymphoid Leukemia, N Engl J Med. Aug. 25, 2011, 365(8): 725-733.
Aziguli Keremu, The construction of rat IL-6 gene siRNA expression vector, Journal of Xinjiang Medical University, Sep. 30, 2007, 29(9), pp. 932-934.
Teoh H.K., Small interfering RNA silencing of interleukin-6 in mesenchymal stromal cells inhibits multiple myeloma cell growth, Leukemia Research, Jan. 31, 2016, vol. 40, pp. 44-53.

*Primary Examiner* — Tracy Vivlemore
(74) *Attorney, Agent, or Firm* — Bayramoglu Law Offices LLC

(57) ABSTRACT

Provided are a siRNA of the human interleukin 6, a recombinant expression CAR-T vector, and a construction method and a use thereof. The siRNA can be used in the treatment of acute B-cell lymphocytic leukemia with CAR19-T for eliminating or alleviating the symptoms of cytokine release syndrome (CRS), and can also be used for alleviating the CRS symptoms caused by treating tumours with CAR-T and even can also be used for alleviating CRS caused by other types of treatment.

20 Claims, 11 Drawing Sheets
Specification includes a Sequence Listing.

SIRNA OF HUMAN IL-6 AND RECOMBINANT EXPRESSION CAR-T VECTOR AND THEIR CONSTRUCTION METHODS AND APPLICATIONS

CROSS REFERENCE TO THE RELATED APPLICATIONS

This application is the national phase entry of International Application No. PCT/CN2016/105263, filed on Nov. 10, 2016, which claims priority from the Chinese patent application no. 201610887703.X filed on Oct. 11, 2016, the entire contents of which are incorporated herein by reference.

TECHNICAL FIELD

This invention belongs to the technical field of tumor immunotherapy, specifically relating to a siRNA of human IL-6, recombinant expression CAR-T vector (especially a CAR-T transgene vector used for the remission of CRS by knocking down IL-6) and their construction methods and applications.

BACKGROUND

The theoretical basis of tumor immunotherapy is that the immune system can identify tumor-associated antigens and regulate the body to attack tumor cells (highly specific cytolysis). In the 1950s, Burnet and Thomas made the theory of "immunological surveillance" that holds that mutational tumor cells that often occur in the body can be identified and eliminated by the immune system, laying a theoretical foundation for tumor immunotherapy [Burnet F M. Immunological aspects of malignant disease. Lancet, 1967; 1: 1171-4]. Then, a host of tumor immunotherapies, including cytokine therapy, monoclonal antibody therapy, adoptive immunotherapy and vaccine therapy, have been applied to clinical practice.

In 2013, CAR-T, a more advanced tumor immunotherapy, was successfully put to clinical use, and showed unprecedented clinical effects. CAR-T is short for Chimeric Antigen Receptor T-Cell Immunotherapy. Clinically, the most leading CAR-T is Novartis' CLT019. For patients with refractory-relapsed acute lymphoblastic leukemia and treated with CLT019, the six-month tumor progression-free survival rate can reach 67%, and the longest response time can be more than two years. By cooperating with hospitals, Shanghai Unicar Biomedical Technology Co., Ltd., a Shanghai-based company, treated 36 patients with refractory-relapsed acute lymphoblastic leukemia, among whom 24 as a percentage of 66.6% experienced complete remission. It's a subversive breakthrough in anti-cancer research. CAR-T may be one of the therapies that are the most likely to cure cancer, and was named the best in top 10 breakthroughs of science and technology 2013 by the journal Science.

In spite of the significant curative effect of CAR-T, in the treatment with the therapy, there may be a special clinical syndrome, of which common clinical manifestations are fever, hypotension, shivering, and a neurological symptom related to a range of significantly elevated cytokine levels in serum and called Cytokine Release Syndrome (CRS). The occurrence mechanism of the syndrome is that after the binding of antigen to T cell receptor, T cell is activated and releases a series of cytokines including IL-6, giving rise to a systematic inflammatory reaction, of which delayed treatment is likely to cause pulmonary edema and then the death of patients (see FIG. 1 for the signaling pathway of IL-6).

Currently, clinically, inflammatory reaction can be inhibited by intravenously injecting antihistamine (such as chlorphenamine maleate), or corticosteroid (such as hydrocortisone); however, correspondingly, CAR-T cell's killing effect on tumor is inhibited, leading to a higher relapse rate of such patients and affecting the curative effect of CAR-T.

Another feasible treatment option is to use commercialized Tocilizumab (Yamero®) to control the occurrence level of CRS. Tocilizumab is human IL-6 receptor monoclonal antibody. The specific binding of Tocilizumab to IL-6 receptor can block IL-6 signal transduction to reduce acute phase reactants, hepcidin products, B cell activation, bone resorption and transformation of cartilage and inhibit the differentiation from T-lymphocyte to Th17 cell to effectively control inflammatory reaction. However, Tocilizumab also has some obvious drawbacks. First, it's very expensive. A Tocilizumab injection for 10 kg of body weight is priced at about RMB 2,000, and an adult patient generally needs 5 ones at a time, which is hard for average families to afford. Second, patients injected with Tocilizumab are vulnerable to infection later in treatment, as their IL-6 receptors are blocked.

Since 1990s, researchers have discovered that double-stranded RNA ("dsRNA") can be used to inhibit the expression of protein. As such ability of silent gene has great potential in the treatment of human diseases, a great many researchers and commercial entities have invested considerable resources in the development of therapies based on the technology.

From a mechanism perspective, after entering plant and invertebrate cells, dsRNA is broken down by Type III endonuclease Dicer into siRNA. [Sharp, RNA interference-2001, Genes Dev. 2001, 15:485]. Type III endonuclease Dicer breaks dsRNA down into siRNA with 2 base bulges and 3' sticky ends. [Bernstein, Caudy, Hammond, & Hannon, Role for a bidentate ribonuclease in the initiation step of RNA interference, Nature 2001, 409:363]. In the integration of siRNA with RNA-induced Silencing Complex (RISC), one or more helicase(s) in RISC unwind(s) double-stranded siRNA, making complementary antisense strands direct target recognition. [Nykanen, Haley, & Zamore, ATP requirements and small interfering RNA structure in the RNA interference pathway, Cell 2001, 107:309]. After the integration with corresponding target mRNA, one or more endonuclease(s) in RISC cleave(s) target mRNA, giving rise to mRNA silencing. [Elbashir, Elbashir, Lendeckel, & Tuschl, RNA interference is mediated by 21- and 22-nucleotide RNAs, Genes Dev 2001, 15:188].

Such interference effect can last long and remain effective after cell division. And RNAi has very good sequence specificity. [Kisielow, M. et al. (2002) Isoform-specific knockdown and expression of adaptor protein ShcA using small interfering RNA, J. of Biochemistry 363: 1-5]. Therefore, RNAi can knock down a type of transcript with its specificity and without affecting other mRNAs with similar sequences. Such features enable siRNA system to show its potential and value in the inhibition of gene expression, gene function research and medicine target validation. In addition, siRNA system can be used to treat relevant diseases, including (1) diseases caused by gene overexpression or misexpression and (2) diseases caused by gene mutation.

SUMMARY

This invention aims to eliminate the drawbacks of existing technology and provide a siRNA of human IL-6, recombinant expression vector and their construction methods and applications.

Purposes of the invention will be achieved with the following technical solutions:

The first purpose of the invention is to provide a siRNA of human IL-6, and the said siRNA is selected from any of the following a-h items:
a. nucleotide sequence as shown in SEQ ID NO: 43 and SEQ ID NO: 44;
b. nucleotide sequence as shown in SEQ ID NO: 45 and SEQ ID NO: 46;
c. nucleotide sequence as shown in SEQ ID NO: 47 and SEQ ID NO: 48;
d. nucleotide sequence as shown in SEQ ID NO: 49 and SEQ ID NO: 50;
e. nucleotide sequence as shown in SEQ ID NO: 51 and SEQ ID NO: 52;
f. nucleotide sequence as shown in SEQ ID NO: 53 and SEQ ID NO: 54;
g. nucleotide sequence as shown in SEQ ID NO: 55 and SEQ ID NO: 56; and
h. nucleotide sequence as shown in SEQ ID NO: 57 and SEQ ID NO: 58.

Further, b. nucleotide sequence as shown in SEQ ID NO: 45 and SEQ ID NO: 46 is preferable.

The second purpose of the invention is to provide the applications of the said siRNA in the preparation of medicine treating or modifying the CRS.

The third purpose of the invention is to provide a recombinant expression vector containing the said siRNA.

Further, the said expression vector is lentiviral expression vector, retroviral expression vector, adenovirus expression vector, adeno-associated virus expression vector or plasmid; lentiviral expression vector containing the said siRNA is preferable.

Further, the said lentiviral expression vector includes the prokaryotic replicon pUC Ori sequence used for plasmid replication, as shown in SEQ ID NO: 2; AmpR sequence with Ampicillin resistance gene and used for the massive proliferation of target strains, as shown in SEQ ID NO: 1; virus-replicon SV40 Ori sequence used for enhancing replication in eukaryocyte, as shown in SEQ ID NO: 3; lentivirus packaging cis element used for lentivirus packaging; ZsGreen1 green fluorescent protein used for eukaryocyte expressing green fluorescence, as shown in SEQ ID NO: 11; IRES ribosome binding sequence used for the common transcription and expression of protein, as shown in SEQ ID NO: 12; human EF1α promoter used for the eukaryotic transcription of chimeric antigen receptor genes, as shown in SEQ ID NO: 14; encoding genes of anti-CD19 chimeric antigen receptors used for making up the second or third generation CAR integrating identification, transmission and promotion, as shown in SEQ ID NO: 52 or SEQ ID NO: 53; enhanced woodchuck hepatitis virus post-transcriptional regulatory element (eWPRE) used for enhancing transgene expression efficiency, as shown in SEQ ID NO: 13; human RNA polymerase III promoter hU6 used for intracellular transcription of siRNA, as shown in SEQ ID NO: 14.

Further, the second generation lentiviral vectors employed by the said lentivirus packaging cis element include lentivirus 5 terminal LTR, as shown in SEQ ID NO: 5, lentivirus 3 terminal Self-Inactivating LTR, as shown in SEQ ID NO: 6, Gag cis element, as shown in SEQ ID NO: 7, RRE cis element, as shown in SEQ ID NO: 8, env cis element, as shown in SEQ ID NO: 9, and cPPT cis element, as shown in SEQ ID NO: 10.

Further, the third generation lentiviral vectors employed by the said lentivirus packaging cis element include lentivirus 5 terminal LTR, as shown in SEQ ID NO: 5, lentivirus 3 terminal Self-Inactivating LTR, as shown in SEQ ID NO: 6, Gag cis element, as shown in SEQ ID NO: 7, RRE cis element, as shown in SEQ ID NO: 8, env cis element, as shown in SEQ ID NO: 9, cPPT cis element, as shown in SEQ ID NO: 10, and RSV promoter, as shown in SEQ ID NO: 4.

Further, the said eWPRE has 6 enhanced nucleotide mutations, which are g.396G>A, g.397C>T, g.398T>C, g.399G>A, g.400A>T, g.411A>T.

Further, the said anti-CD19 chimeric antigen receptors (the second generation CAR) include serialized CD8 leader chimeric receptor signal peptide, as shown in SEQ ID NO: 16, CD19 single-chain antibody light chain VL, as shown in SEQ ID NO: 17, Optimal Linker C, as shown in SEQ ID NO: 18, CD19 single-chain antibody heavy chain VH, as shown in SEQ ID NO: 19, CD8 chimeric receptor hinge, as shown in SEQ ID NO: 20, CD8 chimeric receptor transmembrane, as shown in SEQ ID NO: 21, CD137 chimeric receptor inducible co-stimulater, as shown in SEQ ID NO: 22, and TCR chimeric receptor T cell activation domain, as shown in SEQ ID NO: 23.

Further, the said anti-CD19 chimeric antigen receptors (the third generation CAR) include serialized CD8 leader chimeric receptor signal peptide, as shown in SEQ ID NO: 16, CD19 single-chain antibody light chain VL, as shown in SEQ ID NO: 17, Optimal Linker C, as shown in SEQ ID NO: 18, CD19 single-chain antibody heavy chain VH, as shown in SEQ ID NO: 19, CD8 chimeric receptor hinge, as shown in SEQ ID NO: 20, CD8 chimeric receptor transmembrane, as shown in SEQ ID NO: 21, CD28 chimeric receptor inducible co-stimulater, as shown in SEQ ID NO: 24, CD137 chimeric receptor inducible co-stimulater, as shown in SEQ ID NO: 22, and TCR chimeric receptor T cell activation domain, as shown in SEQ ID NO: 23.

The fourth purpose of the invention is to provide a construction method for recombinant expression vector containing the said siRNA, which involves the following steps:

(1) Storing in the lentiviral skeleton plasmid pLenti-3G silencer the AmpR sequence with Ampicillin resistance gene (as shown in SEQ ID NO: 1), prokaryotic replicon pUC Ori sequence (as shown in SEQ ID NO: 2), virus-replicon SV40 Ori sequence (as shown in SEQ ID NO: 3), lentivirus packaging cis element used for lentivirus packaging, ZsGreen1 green fluorescent protein (as shown in SEQ ID NO: 11), IRES ribosome binding sequence (as shown in SEQ ID NO: 12), enhanced woodchuck hepatitis virus post-transcriptional regulatory element (eWPRE) (as shown in SEQ ID NO: 13), and human RNA polymerase III promoter hU6 (as shown in SEQ ID NO: 14);

(2) Combining the human EF1α promoter (as shown in SEQ ID NO: 15) and anti-CD19 chimeric antigen receptors used for making up the second or third generation CAR integrating identification, transmission and promotion into, and cloning into lentiviral skeleton plasmid through enzyme digestion, ligation and recombination reactions, the design scheme for the second or third generation CAR, to get the recombinant lentiviral plasmid pCAR19-silencer designed with the second or third generation CAR;

(3) Respectively cloning into the recombinant lentiviral plasmid got through step (2) the said siRNA and the negative control sequence as shown in SEQ ID NO: 41 and SEQ ID NO: 42 to get IL-6 knock-down recombinant lentiviral plasmids (pCAR19-1762~pCAR19-1769 and pCAR19-1761 of negative control);

(4) Transfecting recombinant lentiviral plasmids (pCAR19-1761~pCAR19-1769) got through step (3) together with lentiviral packaging plasmids pPac-GP and pPac-R as well as membrane protein plasmid pEnv-G, respectively into HEK293T/17 cell, and collecting supernate containing recombinant lentiviral vectors, which will be released into cell culture supernate if packaging successfully and after gene transcript expression in HEK293T/17 cell; and (5) Respectively getting recombinant lentiviral vectors by purifying recombinant lentivirus supernatant got through step (4) with Ion exchange modes of extraction filtration, adsorption, elution.

Further, in step (1), the second generation lentiviral vectors employed by the said lentivirus packaging cis element, include the lentivirus 5 terminal LTR as shown in SEQ ID NO: 5, lentivirus 3 terminal Self-Inactivating LTR as shown in SEQ ID NO: 6, Gag cis element as shown in SEQ ID NO: 7, RRE cis element as shown in SEQ ID NO: 8, env cis element as shown in SEQ ID NO: 9, and cPPT cis element as shown in SEQ ID NO: 10; the third generation lentiviral vectors employed by the said lentivirus packaging cis element, include the lentivirus 5 terminal LTR as shown in SEQ ID NO: 5, lentivirus 3 terminal Self-Inactivating LTR as shown in SEQ ID NO: 6, Gag cis element as shown in SEQ ID NO: 7, RRE cis element as shown in SEQ ID NO: 8, env cis element as shown in SEQ ID NO: 9, cPPT cis element as shown in SEQ ID NO: 10, and RSV promoter as shown in SEQ ID NO: 4.

Further, in step (2), the said anti-CD19 chimeric antigen receptors used for making up the second generation CAR integrating identification, transmission and promotion, include serialized CD8 leader chimeric receptor signal peptide as shown in SEQ ID NO: 16, CD19 single-chain antibody light chain VL as shown in SEQ ID NO: 17, Optimal Linker C as shown in SEQ ID NO: 18, CD19 single-chain antibody heavy chain VH as shown in SEQ ID NO: 19, CD8 chimeric receptor hinge as shown in SEQ ID NO: 20, CD8 chimeric receptor transmembrane as shown in SEQ ID NO: 21, CD137 chimeric receptor inducible co-stimulater as shown in SEQ ID NO: 22, and TCR chimeric receptor T cell activation domain as shown in SEQ ID NO: 23; the said anti-CD19 chimeric antigen receptors used for making up the third generation CAR integrating identification, transmission and promotion, include serialized CD8 leader chimeric receptor signal peptide as shown in SEQ ID NO: 16, CD19 single-chain antibody light chain VL as shown in SEQ ID NO: 17, Optimal Linker C as shown in SEQ ID NO: 18, CD19 single-chain antibody heavy chain VH as shown in SEQ ID NO: 19, CD8 chimeric receptor hinge as shown in SEQ ID NO: 20, CD8 chimeric receptor transmembrane as shown in SEQ ID NO: 21, CD28 chimeric receptor inducible co-stimulater as shown in SEQ ID NO: 24, CD137 chimeric receptor inducible co-stimulater as shown in SEQ ID NO: 22, and TCR chimeric receptor T cell activation domain as shown in SEQ ID NO: 23.

Further, in step (1), the said eWPRE has 6 enhanced nucleotide mutations, which are g.396G>A, g.397C>T, g.398T>C, g.399G>A, g.400A>T, g.411A>T.

Further, in step (2), the whole CAR gene expression is promoted by human EF1α promoter; located at the N-terminus of CAR coding sequence, CD8 leader chimeric receptor signal peptide is used to direct the localization of CAR protein in cytomembrane; Combined into scfv region, CD19 single-chain antibody light chain VL, Optimal Linker C and CD19 single-chain antibody heavy chain VH are used to identify CD19 antigen; CD8 chimeric receptor hinge is used to anchor scfv in the lateral of cytomembrane; CD8 chimeric receptor transmembrane is used to immobilize the whole chimeric receptor onto cytomembrane; CD137 chimeric receptor inducible co-stimulater is used to stimulate T cell proliferation and cytokine secretion; TCR chimeric receptor T cell activation domain is used to activate the expression of downstream signaling pathway; when scfv region is combined with CD20 antigen, signals are transferred into cells through chimeric receptors to create a series of biological effects including T cell proliferation, increased cytokine secretion, increased anti apoptosis protein, delayed cell death and target cell lysis.

Further, in step (4), the said lentiviral vector has two versions, of which one with fluorescently tagged zsGreen1 is used for in-vitro experiment, while the other without fluorescently tagged zsGreen1 is used for clinical experiment.

Further, in step (4), through the said extraction filtration, the volume of supernatant is controlled at 200 ml~2000 ml, and the vacuum degree of supernatant at −0.5 MPA~−0.9 MPA, to prevent loss of vector caused by plugging holes; through the said extraction filtration adsorption, the PH of solution is controlled at 6-8 to prevent inactivation of vector resulting from changes in PH; through the said elution, the ionic strength of eluant is controlled at 0.5M~1.0M to prevent incomplete elution or inactivation of vector arising out of changes in ionic strength.

The fifth purpose of the invention is to provide the applications of the recombinant expression vector containing the said siRNA in the preparation of a medicine for inflammatory cytokine syndrome caused by the release of IL6 in the treatment with CAR-T.

The sixth purpose of the invention is to provide a kind of CART cell, which is the T lymphocyte modified by the said siRNA.

Another purpose of the invention is to provide the applications of the said CAR-T cell in the preparation of medicines for treating B lymphoma, pancreatic cancer, brain glioma and myeloma.

The invention is to build the human RNA polymerase III promoter hU6, human EF1α promoter, CD8 leader chimeric receptor signal peptide, CD19 single-chain antibody light chain VL, Optimal Linker C, CD19 single-chain antibody heavy chain VH, CD8 chimeric receptor hinge, CD8 chimeric receptor transmembrane, CD137 chimeric receptor inducible co-stimulater and TCR chimeric receptor T cell activation domain into recombinant lentiviral vector to use the human EF1α promoter to turn on the whole CAR gene expression, localize CAR protein on cell surface, identify CD19 antigen, stimulate T cell proliferation, and activate the expression of downstream signaling pathway; when scfv region is combined with CD20 antigen, to transfer signals into cells through chimeric receptors to create a series of biological effects including T cell proliferation, increased cytokine secretion, increased anti apoptosis protein, delayed cell death and target cell lysis; to turn on the expression of siRNA with the human RNA polymerase III promoter hU6, and via RISC complex, to degrade IL-6 mRNA and inhibit the synthesis and secretion of IL-6 to inhibit CRS.

Expression vectors employed by the invention include the prokaryotic replicon pUC Ori used for plasmid replication, pronucleus selection marker AmpR used for the massive proliferation of target strains, virus-replicon SV40 Ori used for enhancing replication in eukaryocyte, lentivirus packaging cis elements (RSV, 5 terminal LTR, 3 terminal Self-Inactivating LTR, Gag, RRE, env, cPPT) used for lentivirus packaging, human RNA polymerase III promoter hU6 used for intracellular transcription of siRNA, eukaryotic fluorescent labeling protein ZsGreen1 used for eukaryocyte expressing green fluorescence, co-expression element IRES used for the common transcription and expression of protein, eukaryotic promoter EF1α used for the eukaryotic transcription of chimeric antigen receptor genes, chimeric antigen receptors (CD8 leader, CD19 VL, Optimal Linker C (SEQ ID NO: 19), CD19 VH, CD8 Hinge, CD8 Transmembrane, CD137, TCR) used for making up the second and third generations of CAR integrating identification, transmission and promotion, and post-transcriptional regulatory element eWPRE used for enhancing transgene expression efficiency.

The invention involves peptide-containing pharmaceutical preparations, including:

1. Recombinant lentiviral vector skeleton made up of the human RNA polymerase III promoter hU6, AmpR sequence with Ampicillin resistance gene, prokaryotic replicon pUC Ori sequence, virus-replicon SV40 Ori sequence, RSV promoter, human EF1α promoter, lentivirus 5 terminal LTR, lentivirus 3 terminal Self-Inactivating LTR, Gag cis element, RRE cis element, env cis element, cPPT cis element, ribosome binding sequence IRES, ZsGreen1 green fluorescent protein, and woodchuck hepatitis virus post-transcriptional regulatory element (WPRE), which skeleton can carry different therapeutic genes and be widely used in adoptive cell therapy, and carry different siRNAs and be widely used in the treatment of diseases caused by gene overexpression, mixexpression and mutation.

2. Composing recombinant lentiviral vector of recombinant lentiviral vector skeleton, IL6-siRNA, CD8 leader chimeric receptor signal peptide, CD19 single-chain antibody light chain VL, Optimal Linker C, single-chain antibody hinge Linker A, single-chain antibody hinge Linker B, single-chain antibody hinge Linker C, CD19 single-chain antibody heavy chain VH, CD8 chimeric receptor hinge, CD8 chimeric receptor transmembrane, CD28 chimeric receptor inducible co-stimulater, CD137 chimeric receptor inducible co-stimulater and TCR chimeric receptor T cell activation domain, by which recombinant lentiviral vectors got can realize the expression of CD19 chimeric antigen receptors on human T lymphocytes, guide and activate the cytotoxicity of T lymphocyte on CD19 positive cell, and be used to clinically treat B lymphocytic leukemia, B lymphoma and multiple myeloma. Expressing the siRNA of IL-6 in human T lymphocyte can effectively reduce the expression level of IL-6, and be used to ease the Cytokine Release Syndrome (CRS).

siRNA sequence designed by the invention contains 21-bp nucleotide and employs the oligonucleotide pattern of N2[CG]N8[AU]N8[AU]N2. Stem-loop splicing hpRNA is employed between complementary sequences. The success rate of siRNA design has been greatly improved through the screening of siRNA pattern, GC percentage, T or A or G in a row, consecutiver GC, 3' end nt pattern, thermodynamic value, siRNA target, identity, alignment and other conditions.

In the T cell cytotoxicity assay, the system in which the human RNA polymerase III promoter hU6 transcripts siRNA to inhibit the expression of IL-6 employed by the invention, was found to be able to effectively inhibit the transcriptional level of mRNA upon QPCR test and effectively decrease the expression level of IL-6 in cell culture supernatant upon CBA test, and can inhibit the expression level of IL-6 in vivo and ease the symptoms of the CRS in the future.

The invention delivers siRNAs by means of lentiviral vectors (see FIG. 2). Firstly, it saves costs and prevents the expensive cost of siRNA synthesis in vitro; secondly, it avoids inefficient delivery of siRNA in vivo; thirdly, it uses the human RNA polymerase III promoter hU6 to express siRNAs, which can effectively utilize intracellular RNA transcription system, highly express corresponding siRNAs and achieve good gene silencing efficacy through a series of enzymatic actions.

The vector skeleton employed by the invention is the third generation lentiviral vector (see FIG. 3A) 3' SIN LTR, from which U3 area is removed, eliminating the possibility of the self-replication of lentiviral vector and greatly increasing security, which includes elements cPPT and WPRE, strengthening the efficiency of transduction and transgene expression, and which employs RSV promoter, ensuring the continuous and efficient transcription of core RNA in lentiviral vector packaging, which employs the human EF1α promoter, so that CAR gene can be continuously expressed in vivo for a long time.

The siRNA knock-down scheme employed by the invention can also be applied to the third generation CAR design scheme. Over the second generation design, the third generation CAR includes CD28 chimeric receptor inducible co-stimulater (SEQ ID NO: 24).

The lentiviral vector column purification system employed by the invention (see FIG. 8) is a lentivirus scale production process developed by the company. The common supercentrifugation or ultracentrifugation method segregates lentiviral particles with the principle of centrifugal sedimentation, which will inevitably leave a lot of impurities of similar sedimentation coefficient and adversely affect follow-up experiments. Also, the complex tubing process, cumbersome operations and multiple container transformations will increase the risk of contamination. However, the lentiviral vector column purification process employed by the invention is semi-automatic and entirely done in one-hundred-grade experimental region, avoiding cumbersome manual operations and risk of contamination and retrieving lentiviral vectors completely meeting clinical standards in endotoxin, *mycoplasma* and other indicators. The development of fully automatic purifier may be followed up.

The CAR design scheme employed by the invention can also be applied to the structure of the second generation lentiviral vector. The major difference in structure between the second and third generation lentiviral vectors (see FIG. 3B) is that the third generation lentiviral vector replaces the U3 area of the second vector 5'LTR with RSV promoter to eliminate dependency on Tat protein in U3 transcription to remove Tat sequence from the structural gene of lentivirus and improve the transcriptional level and continuity of lentiviral genome. The second generation lentiviral vector is mainly different from the third one in the transcriptional method of genome, and thus the CAR design scheme employed by the invention can be applied to the two generations of lentiviral vectors.

The third generation lentiviral skeleton plasmid involved in the invention employs enhanced WPRE, which, compared to the WPRE employed by Carl H. June and others at the University of Pennsylvania (Porter D L, Levine B L, Kalos M, Bagg A, June C H. Chimeric antigen receptormodified T cells in chronic lymphoid leukemia. N Engl J Med 2011; 365:725-33.), has 6 enhanced nucleotide mutations (g.396G>A, g.397C>T, g.398T>C, g.399G>A, g.400A>T, g.411A>T), and can strengthen the polyadenylation of primary transcripts, intracellular content of mRNA and transgenic expression efficiency.

The Lentival packaging system involved in the invention is a four-plasmid packaging system without helper virus, which produces recombinant lentiviral vectors by transfecting four plasmids into HEK293T/17 cells. Recombined lentiviral vector is a replication-defective vector that can integrate foreign fragments into host gene, is disposable and can't be replicated or proliferated, thereby greatly increasing security.

The lentiviral vector employed by the invention has two versions, of which one with fluorescently tagged zsGreen1 is used for in-vitro experiment, while the other without fluorescently tagged zsGreen1 is used for clinical experiment.

The Linker design for scfv employed by the invention can significantly improve cytokine secretion, as well as the cytotoxicity in vitro and clinical treatment effect of CAR-T cell.

It can be seen that recombinant lentiviral vectors said in the invention can give reliable transgenic guarantee for the CAR-T treatment of B lineage acute lymphoblastic leukemia (ALL), significantly lowering the risk of CRS and relieving patients' pain.

IL-6 know-down siRNA expression cassette and its siRNA expression products described in the invention can be used not only in CAR19-T treatment of acute B lymphocytic leukemia (ALL) to eliminate or alleviate the symptoms of CRS, but also to relieve CRS symptoms caused by CAR-T treatment for all types of tumors such as B-lymphoma, pancreatic cancer, brain glioma, bone cancer, even can be used to relieve CRS caused by other types of therapy.

BRIEF DESCRIPTION OF THE DRAWINGS

FIG. 7A shows the sequencing alignment result of pCAR19-1761;

FIG. 7B shows the sequencing alignment result of pCAR19-1762;

FIG. 7C shows the sequencing alignment result of pCAR19-1763;

FIG. 7D shows the sequencing alignment result of pCAR19-1764;

FIG. 7E shows the sequencing alignment result of pCAR19-1765;

FIG. 7F shows the sequencing alignment result of pCAR19-1766;

FIG. 7G shows the sequencing alignment result of pCAR19-1767;

FIG. 7H shows the sequencing alignment result of pCAR19-1768;

FIG. 7I shows the sequencing alignment result of pCAR19-1769;

FIGS. 12A and 12B show a WB detection chart of CAR protein expression. FIG. 12 B are the beta-actin bands;

FIG. 13A is the CBA detection result of 4 h; FIG. 13B is the CBA detection result of 24 h;

DETAILED DESCRIPTION OF THE EMBODIMENTS

Figure 1:
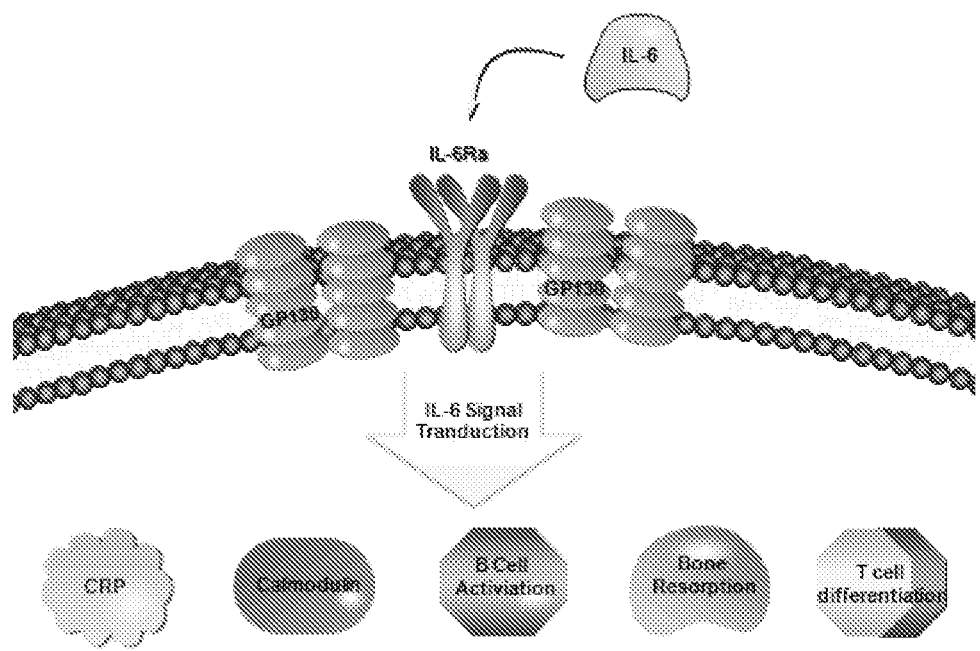
FIG. 1 is a schematic diagram of IL-6 signaling pathway described in the invention.
Figure 2:
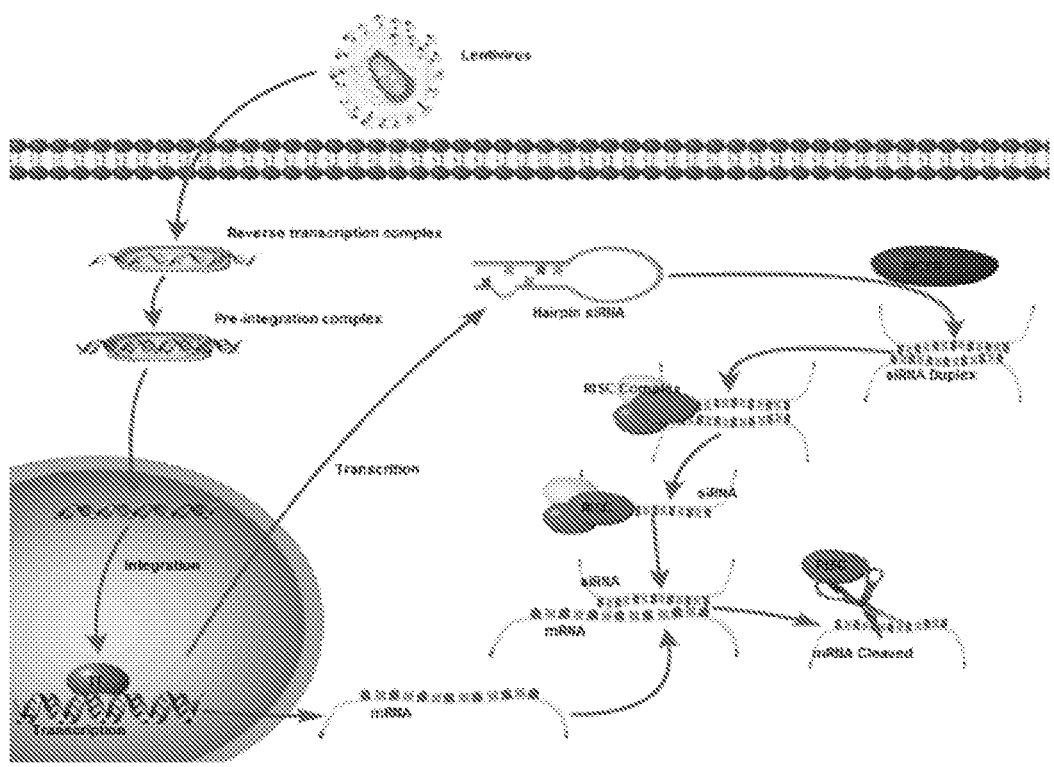
FIG. 2 is a schematic diagram of siRNA delivery by lentivirus described in the invention.
Figure 3:
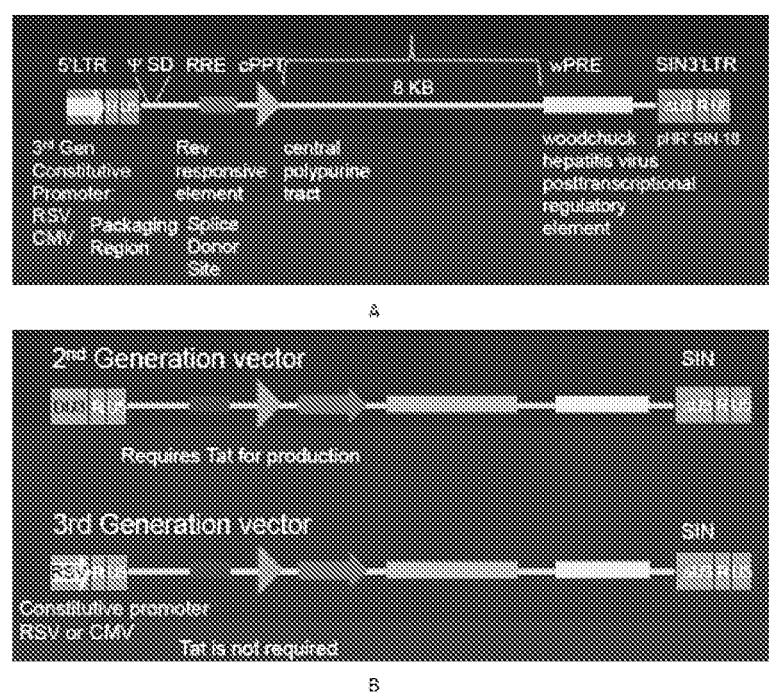
FIG. 3A is a structure diagram of the $3^{rd}$ generation lentiviral vector adopted by the invention.
FIG. 3B is a comparison between the $2^{nd}$ generation and $3^{rd}$ generation lentiviral vector structure.

The following embodiments are only to illustrate the invention not to limit its scope. An experimental method without specific conditions stated in an embodiment is generally in accordance with conventional conditions or conditions recommended by the manufacturer.

Embodiment 1 To Construct Recombinant Lentiviral Vector

I. Material

1. Lentiviral cytoskeleton plasmid pLenti-3G silencer, lentiviral packaging plasmid pPac-GP, pPac-R and membrane protein plasmid pEnv-G, HEK293T/17 cells, homologous recombinase, Oligo Annealing Buffer were provided by Shiao (Shanghai) Biotech Co., Ltd.;

2. Primers: Primers required for amplification of DNA fragments and target sites were designed according to the principle of primer design, specifically as follows:

EF1α-F:
(SEQ ID NO: 25)
5'-attcaaaattttatcgatgctccggtgcccgtcagt-3'

EF1α-R:
(SEQ ID NO: 26)
5'-TCACGACACCTGAAATGGAAGA-3'

CD8 leader-F:
(SEQ ID NO: 27)
5'-ggtgtcgtgaggatccgccaccatggccttaccagtgaccgc-3'

CD8 leader-R:
(SEQ ID NO: 28)
5'-GTGTCATCTGGATGTCCGGCCTGGCGGCGTG-3'

VL-F:
(SEQ ID NO: 29)
5'-cacgccgccaggccggacatccagatgacacagactacatc-3'

VL-R:
(SEQ ID NO: 30)
5'-TGTGATCTCCAGCTTGGTCC-3'

OLC-VH-F:
(SEQ ID NO: 31)
5'-caagctggagatcacaggtggcggtggctcgggcggtggtgggtcgggtggcggcggatctgaggtgaaactgcaggagtca-3'

CH-R:
(SEQ ID NO: 32)
5'-TGAGGAGACGGTGACTGAGGT-3'

CD8 Hinge-F:
(SEQ ID NO: 33)
5'-AGTCACCGTCTCCTCAACCACGACGCCAGCGCC-3'

CD8 Hinge-R:
(SEQ ID NO: 34)
5'-GTAGATATCACAGGCGAAGTCCA-3'

CD8 Transmembrane-F:
(SEQ ID NO: 35)
5'-cgcctgtgatatctacatctgggcgcccttggc-3'

CD8 Transmembrane-R:
(SEQ ID NO: 36)
5'-TCTTTCTGCCCCGTTTGCAGTAAAGGGTGATAACCAGTG-3'

CD137-F:
(SEQ ID NO: 37)
5'-aaacggggcagaaagaaactc-3'

CD137-R:
(SEQ ID NO: 38)
5'-TGCTGAACTTCACTCTCAGTTCACATCCTCCTTCTTCTTC-3'

TCR-F:
(SEQ ID NO: 39)
5'-agagtgaagttcagcaggagcg-3'

TCR-R:
(SEQ ID NO: 40)
5'-GGAGAGGGGCGTCGACTTAGCGAGGGGGCAGGGC-3' siRNA1761-F (negative control):
(SEQ ID NO: 41)
5'-CCGGTTCTCCGAACGTGTCACGTCTCGAGACGTGACACGTTCGGAGAATTTTTG-3' siRNA1761-R (negative control):
(SEQ ID NO: 42)
5'-AATTCAAAAATTCTCCGAACGTGTCACGTCTCGAGACGTGACACGTTCGGAGAA-3' siRNA1762-F:
(SEQ ID NO: 43)
5'-CCGGGTGAAGCTGAGTTAATTTATGCTCGAGTAAATTAACTCAGCTTCACATTTTTTG-3' siRNA1762-R:
(SEQ ID NO: 44)
5'-AATTCAAAAAAATGTGAAGCTGAGTTAATTTACTCGAGCATAAATTAACTCAGCTTCAC-3' siRNA1763-F:
(SEQ ID NO: 45)
5'-CCGGGCACAGAACTTATGTTGTTCTCGAGAACAACATAAGTTCTGTGCCCTTTTTTG-3' siRNA1763-R:
(SEQ ID NO: 46)
5'-AATTCAAAAAAGGGCACAGAACTTATGTTGTTCTCGAGAGAACAACATAAGTTCTGTGC-3' siRNA1764-F:
(SEQ ID NO: 47)
5'-CCGGCTCAGATTGTTGTTGTTAATGCTCGAGTTAACAACAACAATCTGAGGTTTTTTG-3' siRNA1764-R:
(SEQ ID NO: 48)
5'-AATTCAAAAAAACCTCAGATTGTTGTTGTTAACTCGAGCATTAACAACAACAATCTGAG-3' siRNA1765-F:
(SEQ ID NO: 49)
5'-CCGGGCAGCTTTAAGGAGTTCCTGCCTCGAGAGGAACTCCTTAAAGCTGCGCTTTTTTG-3' siRNA1765-R:
(SEQ ID NO: 50)
5'-AATTCAAAAAAGCGCAGCTTTAAGGAGTTCCTCTCGAGGCAGGAACTCCTTAAAGCTGC-3' siRNA-1766-F:
(SEQ ID NO: 51)
5'-CCGGGTGTAGGCTTACCTCAAATAACTCGAGATTTGAGGTAAGCCTACACTTTTTTTG-3' siRNA1766-R:
(SEQ ID NO: 52)
5'-AATTCAAAAAAAGTGTAGGCTTACCTCAAATCTCGAGTTATTTGAGGTAAGCCTACAC-3'

-continued siRNA1767-F:
(SEQ ID NO: 53)
5'-CCGGCTCAAATAAATGGCTAACTTACTCGAGAGTTAGCCATTTATTT
GAGGTTTTTTG-3' siRNA1767-R:
(SEQ ID NO: 54)
5'-AATTCAAAAAACCTCAAATAAATGGCTAACTCTCGAGTAAGTTAGC
CATTTATTTGAG-3' siRNA1768-F:
(SEQ ID NO: 55)
5'-CCGGGATGCTTCCAATCTGGATTCACTCGAGAATCCAGATTGGAAGC
ATCCATTTTTG-3' siRNA1768-R:
(SEQ ID NO: 56)
5'-AATTCAAAAAATGGATGCTTCCAATCTGGATTCTCGAGTGAATCCAG
ATTGGAAGCATC-3' siRNA1769-F:
(SEQ ID NO: 57)
5'-CCGGCTTCCAATCTGGATTCAATGACTCGAGATTGAATCCAGATTGG
AAGCATTTTTG-3' siRNA1769-R:
(SEQ ID NO: 58)
5'-AATTCAAAAAATGCTTCCAATCTGGATTCAATCTCGAGTCATTGAAT
CCAGATTGGAAG-3'

WPRE-QPCR-F:
(SEQ ID NO: 59)
5'-CCTTTCCGGGACTTTCGCTTT-3'

WPRE-QPRC-R:
(SEQ ID NO: 60)
5'-GCAGAATCCAGGTGGCAACA-3'

Actin-QPCR-F:
(SEQ ID NO: 61)
5'-CATGTACGTTGCTATCCAGGC-3'

Actin-QPCR-R:
(SEQ ID NO: 62)
5'-CTCCTTAATGTCACGCACGAT-3'

CAR-QPCR-F:
(SEQ ID NO: 63)
5'-GACTTGTGGGGTCCTTCTCCT-3'

CAR-QPCR-R:
(SEQ ID NO: 64)
5'-GCAGCTACAGCCATCTTCCTC-3'

IL6-QPCR-F:
(SEQ ID NO: 65)
5'-GGATTCAATGAGGAGACTT-3'

IL6-QPCR-R:
(SEQ ID NO: 66)
5'-ATCTGTTCTGGAGGTACT-3'

3. The DNA sequences shown in SEQ ID NO: 15~SEQ ID NO: 66 were synthesized by Shanghai Generay Biotech Co., Ltd., and stored as oligonucleotide dry powder or plasmid;

4. Tool enzymes BspE I, EcoR I, BamH I, Kpn I, Cla I and T4 DNA ligases were purchased from NEB;

5. PrimerSTAR HS DNA Polymerase, RN were purchased from Takara;

6. 0.22 μm-0.8 μm PES filters were purchased from millipore;

7. The Plasmid Extraction Kit and Agarose Gel Recovery Kit were purchased from MN;

8. TOP 10 Competent Cell were purchased from tiangen;

9. NaCl, KCl, Na$_2$HPO$_4$.12H$_2$O, KH$_2$PO$_4$, Trypsin, EDTA, CaCl$_2$), NaOH, PEG6000 were purchased from Shanghai Sangon Biotech;

10. Opti-MEM, FBS, DMEM, 1640, Pen-Srep, Hepes were purchased from invitrogen;

11. Biotinylated protein L was purchased from GeneScript;

12. HRP-labeled secondary antibodies and DAB working fluid were purchased from ZSGB-BIO;

13. ECL+Plus™ Western blotting system was purchased from Amersham;

14. DNeasy kit was purchased from Shanghai Generay Biotech Co., Ltd.;

15. Lymphocyte Separation Medium were purchased from Dakewe Biotech Co., Ltd.;

16. Phycoerythrin (PE)-conjugated streptavidin, CBA kit were purchased from BD Bioscience;

17. SA-HRP were purchased from Yeasen Biotech Co., Ltd.;

18. *Mycoplasma* Detection Kit, Endotoxin Detection Kit and CD19$^+$K562 Cell were purchased from Shiao (Shanghai) Biotech Co., Ltd.;

19. LDH Detection Kit were purchased from promega;

II. Construction Method of Recombinant Lentiviral Vector lvCAR19-1761~lvCAR19-1769.

Figure 4:
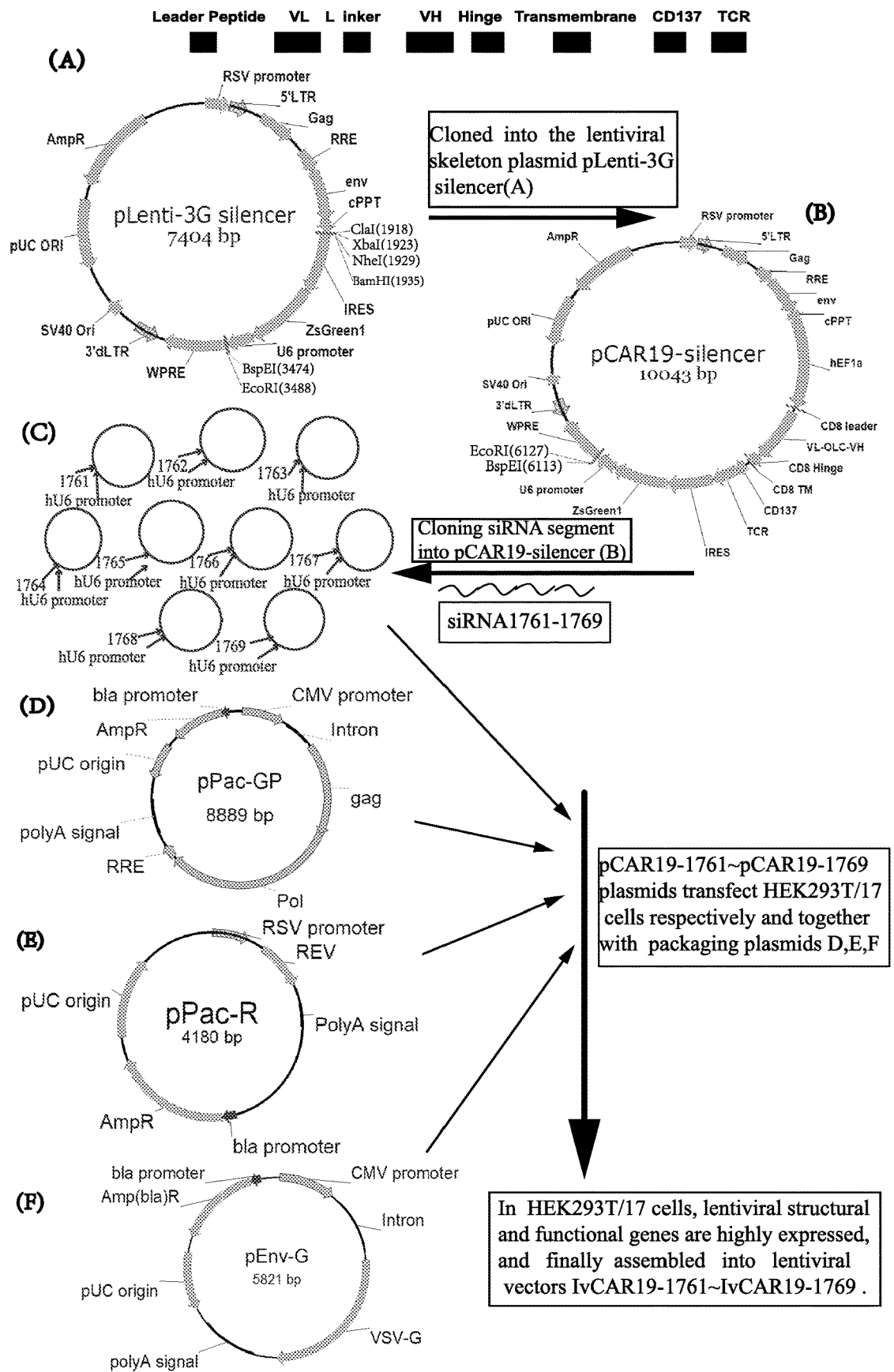
FIG. 4 is a flowchart of the construction of the recombinant lentiviral vector described in the invention; Among them, (A) is a structure diagram of lentiviral cytoskeleton plasmid pLenti-3G silencer; (B) is a structure diagram of pCAR19-silencer plasmid; (C) is a schematic diagram of pCAR19-1761~pCAR19-1769 plasmid; (D) is a structure diagram of lentiviral packaging plasmid pPac-GP; (E) is a structure diagram of lentiviral packaging plasmid pPac-R; (F) is a structure diagram of membrane protein pEnv-G.

See FIG. 4. The construction method of the recombinant lentiviral vector described in the invention is as follows:

1. The human EF1α promoters, CD8 leader chimeric receptor signal peptide, CD19 single chain antibody light chain VL, Optimal Linker C, CD19 single chain antibody heavy chain VH, CD8 chimeric receptor hinge, CD8 transmembrane transmembrane domain chimeric receptor, the chimeric receptor co-stimulation factor—CD137, TCR and T cell activation domain chimeric receptor fragments were cloned into the lentiviral cytoskeleton plasmid pLenti-3G silencer to obtain recombinant lentiviral plasmid pCAR19-silencer, and the siRNA fragments were connected into pCAR19-silencer respectively to obtain IL-6 know-down recombinant lentiviral plasmid pCAR19-1761~pCAR19-1769.

Figure 5:
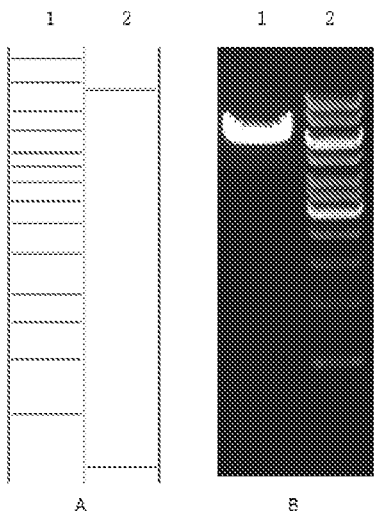
FIG. 5A is the schematic diagram of the restriction enzyme digestion prediction of lentiviral cytoskeleton plasmid pLenti-3G silencer; of which lane 1 is 1 kb DNA ladder Marker: the bands from top to bottom are: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane 2 is the Cla I+BamH I digestion prediction of pLenti-3G silencer: the bands from top to bottom are: 7381 bp, 23 bp.
FIG. 5B is the enzymatic cleavage agarose gel electrophoregram of lentiviral cytoskeleton plasmid pLenti-3G silencer, and lane 1 is the result of Cla I+BamH I digestion of pLenti-3G silencer; lane 2 is the result of electrophoresis of 1 kb DNA ladder Marker.

(1) The lentiviral cytoskeleton plasmid pLenti-3G silencer was double digested with Cla I and BamH I restriction enzymes. The product was electrophoresed on a 1.5% agarose gel to confirm the 7381 bp fragment V1 (see FIG. 5), then such gel was recovered and placed in an Eppendorf tube. The corresponding fragments were recovered with Agarose Gel Recovery Kit of MN (see Table 1), and the purity and concentration of the product were determined;

TABLE 1

| | |
|---|---|
| 1. Sol | Add the sol solution in a ratio of 200 μl NTI/100 mg gel, and place it in a 50° C. water bath for 5-10 minutes. |
| 7. Bind to DNA | Centrifuge at 11,000 g for 30 seconds, and discard the filtrate. |
| 8. Wash membrane | Add 700 μl NT3, centrifuge at 11,000 g for 30 seconds, and discard the filtrate |
| 9. Wash membrane | Repeat the third step once |
| 10. Dry | Centrifuge at 11,000 g for 1 minute, replace with a new collection tube, and leave it at room temperature for 1 minute. |
| 11. Elute DNA | Add 15-30 μl NE, leave it at room temperature for 1 minute, centrifuge at 11,000 g for 1 minute, and then collect the filtrate. |

Table 1 Procedures for the Recovery of Agarose Gels (2) Use the primers EF1α-F and EF1α-R with the synthesized SEQ ID NO: 15 as a template, and apply the system in Table 2. PCR circulation condition was: 98° C. 3 min, (98° C. 10 sec, 55° C. 15 sec, 72° C. 2 min)*35 cycle, 72° C. 10 min. The product was electrophoresed on a 1.5% agarose gel to confirm the 1208 bp fragment a, then such gel was recovered and placed in an Eppendorf tube. The corresponding fragments were recovered with Agarose Gel Recovery Kit of MN (see Table 1), and the purity and concentration of the product were determined;

TABLE 2

| Reagent | Volume (µl) |
| --- | --- |
| H₂O | 32.5 |
| 5 × Buffer (with Mg2+) | 10 |
| dNTP (2.5 mM each) | 4 |
| Primer1 (+)(10 µM) | 1 |
| Primer2 (−)(10 µM) | 1 |
| Template | 1 |
| PrimeSTAR | 0.5 |

Table 2 50 µl PCR Reaction System (3) Use the primers CD8 leader-F and CD8 leader-R with the synthesized SEQ ID NO: 16 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 101 bp fragment b, then such gel was recovered and placed in an Eppendorf tube. The corresponding fragments were recovered with Agarose Gel Recovery Kit of MN (see Table 1), and the purity and concentration of the product were determined;

(4) Use the primers VL-F and VL-R with the synthesized SEQ ID NO: 17 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 336 bp fragment c, then such gel was recovered and placed in an Eppendorf tube. The corresponding fragments were recovered with Agarose Gel Recovery Kit of MN (see Table 1), and the purity and concentration of the product were determined;

(5) Use the primers OLC-VH-F and VH-R with the synthesized SEQ ID NO: 19 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 421 bp fragment d, then such gel was recovered and placed in an Eppendorf tube. The corresponding fragments were recovered with Agarose Gel Recovery Kit of MN (see Table 1), and the purity and concentration of the product were determined;

(6) Use the primers CD8 Hinge-F and CD8 Hinge-R with the synthesized SEQ ID NO: 20 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 147 bp fragment e, then such gel was recovered and placed in an Eppendorf tube. The corresponding fragments were recovered with Agarose Gel Recovery Kit of MN (see Table 1), and the purity and concentration of the product were determined;

(7) Use the primers CD8 Transmembrane-F and CD8 Transmembrane-R with the synthesized SEQ ID NO: 21 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 100 bp fragment f, then such gel was recovered and placed in an Eppendorf tube. The corresponding fragments were recovered with Agarose Gel Recovery Kit of MN (see Table 1), and the purity and concentration of the product were determined;

(8) Use the primers CD137-F and CD137-R with the synthesized SEQ ID NO: 22 as a template, and apply the system in Table 2. PCR circulation condition was: 98° C. 3 min, (98° C. 10 sec, 55° C. 15 sec, 72° C. 30 sec)*35 cycle, 72° C. 5 min.

The product was electrophoresed on a 1.5% agarose gel to confirm the 142 bp fragment g, then such gel was recovered and placed in an Eppendorf tube. The corresponding fragments were recovered with Agarose Gel Recovery Kit of MN (see Table 1), and the purity and concentration of the product were determined;

(9) Use the primers TCR-F and TCR-R with the synthesized SEQ ID NO: 23 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 335 bp fragment h, then such gel was recovered and placed in an Eppendorf tube. The corresponding fragments were recovered with Agarose Gel Recovery Kit of MN (see Table 1), and the purity and concentration of the product were determined;

(10) Applying the system in Table 3, 1 µl each of DNA fragments b, c and d were taken as templates to add to Eppendorf tubes except for primers. PCR circulation condition was: 98° C. 3 min, (98° C. 10 sec, 60° C. 10 sec, 72° C. 40 sec)*6 cycle. To add primer CD8 leader-F/VH-R with the conditions as (98° C. 10 sec, 60° C. 10 sec, 72° C. 40 sec)*24 cycle, 72° C. 5 min. The product was electrophoresed on a 1.5% agarose gel to confirm the 814 bp fragment i, then such gel was recovered and placed in an Eppendorf tube. The corresponding fragments were recovered with Agarose Gel Recovery Kit of MN (see Table 1), and the purity and concentration of the product were determined;

TABLE 3

| Reagent | Volume (µl) |
| --- | --- |
| H₂O | 33.5-1* number of templates |
| 5 × Buffer (with Mg2+) | 10 |
| dNTP (2.5 mM each) | 4 |
| Primer1 (+)(10 µM) | 1 |
| Primer2 (−)(10 µM) | 1 |
| Template | 1* number of templates |
| PrimeSTAR | 0.5 |

Table 3 50 µl Overlapping PCR Reaction System

(11) Applying the system in Table 3, 1µl each of DNA fragments e, f, g and h were taken as templates to add to Eppendorf tubes except for primers. PCR circulation condition was: 98° C. 3 min, (98° C. 10 sec, 60° C. 10 sec, 72° C. 40 sec)*6 cycle. To add primer CD8 Hinge-F/TCR-R with the conditions as (98° C. 10 sec, 60° C. 10 sec, 72° C. 40 sec)*24 cycle, 72° C. 5 min. The product was electrophoresed on a 1.5% agarose gel to confirm the 704 bp fragment j, then such gel was recovered and placed in an Eppendorf tube. The corresponding fragments were recovered with Agarose Gel Recovery Kit of MN (see Table 1), and the purity and concentration of the product were determined;

(12) The DNA fragments V1, a, i, j were added to the Eppendorf tubes in a total volume of 5 μl with a molar ratio of 1:1:1:1. 15 μl of the homologous recombinase reaction solution was added to the tubes, and the mixtures were incubated at 42° C. for 30 minutes. Place them on ice for 2-3 minutes. Add the reaction solution to 50 μl of TOP10, gently rotate to mix the contents, place them on ice for 30 minutes, then put the tubes in the thermostatic water bath pre-warmed to 42° C. for 90 seconds, and quickly transfer the tubes in an ice bath. The cells were allowed to cool for 2-3 minutes. Add 900 μl of LB medium to each tube, then put the tubes to a 37° C. shaker and incubate for 1 hour to resuscitate the bacteria. Take 100 μl of transformant bacteria solution to apply to an Amp LB agar plate, invert the plate, and culture in a thermostatic incubator at 37° C. for 16 hours.

Figure 6:
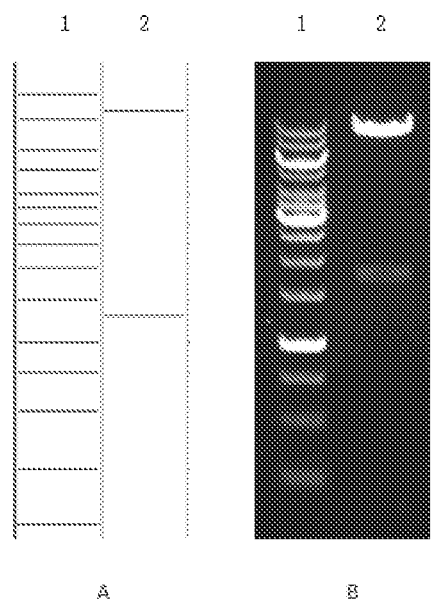
FIG. 6A is the schematic diagram of the restriction enzyme digestion prediction of recombinant lentiviral plasmid pCAR19-silencer, of which lane 1 is 1 kb DNA ladder Marker: the bands from top to bottom are: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane 2 is the Kpn I digestion prediction of pCAR19-silencer: the bands from top to bottom are: 8335 bp, 1708 bp.
FIG. 6B the enzymatic cleavage agarose gel electrophoregram of recombinant lentiviral plasmid pCAR19-silencer, and lane 1 is the result of electrophoresis of 1 kb DNA ladder Marker; lane 2 is the result of Kpn I digestion of pCAR19-silencer.

The clones were picked for colony PCR identification, and the correct clones were identified as recombinant lentiviral plasmid pCAR19-silencer. Enzyme digestion identification was performed for the correct clones (see FIG. 6);

(13) The recombinant lentiviral plasmid pCAR19-silencer was double digested with BspE I and EcoR I restriction enzymes. The product was electrophoresed on a 1.5% agarose gel to confirm the 10029 bp fragment V2, then such gel was recovered and placed in an Eppendorf tube. The corresponding fragments were recovered with Agarose Gel Recovery Kit of MN (see Table 1), and the purity and concentration of the product were determined;

(14) The synthesized siRNA1761-F/R~siRNA1769-F/R were dissolved into 20 μM with oligo annealing buffer respectively, and each 30 μl of the corresponding F and R were mixed. The mixture of siRNA1761-F&R~siRNA1769-F&R was heated in a water bath at 95° C. for 5 minutes, and then the water bath was opened and allowed to cool to room temperature to form double-stranded oligonucleotide fragments. Take 1 μl for the ligation reaction (see Table 4), ligate at 4° C. for 16 h, and then place it on ice for 2-3 minutes. Add the reaction solution to 50 μl of TOP10, gently rotate to mix the contents, place them on ice for 30 minutes, then put the tubes in the thermostatic water bath pre-warmed to 42° C. for 90 seconds, and quickly transfer the tubes in an ice bath. The cells were allowed to cool for 2-3 minutes. Add 900 μl of LB medium to each tube, then put the tubes to a 37° C. shaker and incubate for 1 hour to resuscitate the bacteria. Take 100 μl of transformant bacteria solution to apply to an Amp LB agar plate, invert the plate, and culture in a thermostatic incubator at 37° C. for 16 hours.

Figures 7, 8:
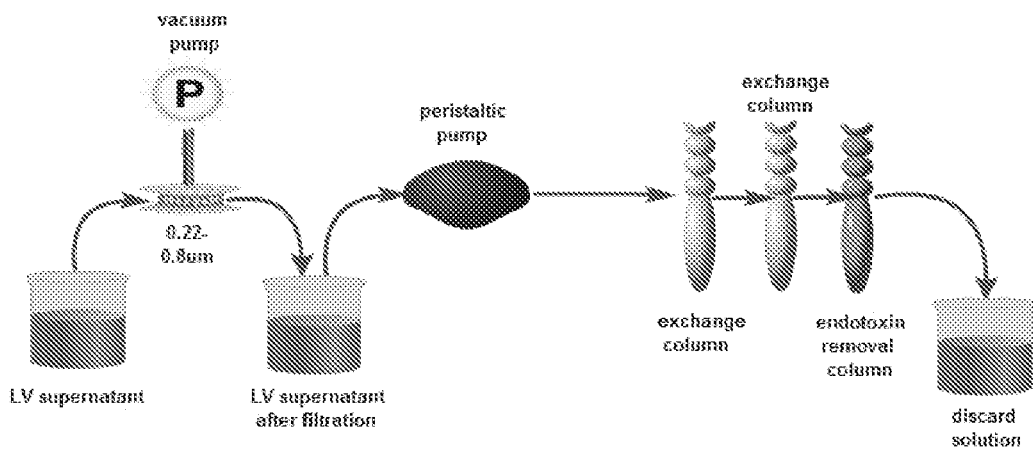
FIG. 8 is a flowchart of ion exchange chromatography for purification of recombinant lentiviral vectors.

The clones were picked for colony PCR identification, and the correct clones were identified as IL-6 know-down recombinant lentiviral plasmid pCAR19-1761~pCAR19-1769. The correct clones were sequenced and identified (see FIG. 7).

TABLE 4

| Reagent | Volume (μl) |
| --- | --- |
| H$_2$O | 13 |
| V2 | 3 |
| 10 × T4 DNA ligase Buffer | 2 |
| T4 DNA ligase | 1 |
| Annealed double-stranded oligonucleotides | 1 |

Table 4 20 μl Ligation Reaction System

2. Packaging of Recombinant Lentiviral Vector lvCAR19-1761~lvCAR19-1769

(1) Complete medium: take out the pre-warmed fresh medium, add 10% FBS +5 ml Pen-Srep, and mix them upside down;

(2) 1×PBS solution: weigh 8 g of NaCl, 0.2 g of KCl, 3.58 g of Na$_2$HPO$_4$.12H$_2$O, 0.24 g of KH$_2$PO4, and put them in a 1000 ml beaker, and add 900 ml of Milli-Q grade ultrapure water to dissolve. After completion of the dissolution, the volume was adjusted to 1000 ml using a 1000 ml measuring cylinder, and the mixture was sterilized by heat sterilization at 121° C. for 20 minutes;

(3) 0.25% Trypsin solution: weigh 2.5 g of Trypsin, 0.19729 g EDTA, and put them in a 1000 ml beaker, and add 900 ml of 1×PBS solution to dissolve. After completion of the dissolution, the volume was adjusted to 1000 ml using a 1000 ml measuring cylinder, and the mixture was sterilized via 0.22 μM filter. It could be saved in the refrigerator at −20° C. for long-term use;

(4) 0.5M CaCl2 solution: weigh 36.75 g of CaCl2, and dissolve it with 400 ml of Milli-Q grade ultrapure water; The volume was adjusted to 500 ml with Milli-Q grade ultrapure water, and mixed; The mixture was sterilized via 0.22 μM filter, and stored in 50 ml centrifuge tubes with about 45 ml in each tube at 4° C.

(5) 2×HBS solution: weigh 4.09 g of NaCl, 0.269 g of Na$_2$HPO4, 5.96 g of Hepes, and dissolve them with 400 ml Milli-Q grade ultrapure water; After calibrating the PH meter, the PH of the FIBS solution was adjusted to 7.05 with 2M NaOH solution. It was about 3 ml of 2M NaOH to consume to adjust the PH of each bottle of HBS.

(6) The frozen HEK293T/17 cells were removed from the liquid nitrogen container and repidly transferred to a 37° C. water bath for 1-2 minutes, and then put them on a super clean bench. Aseptically transfer all the liquid in the freezing tube to a 10 cm$^2$ petri dish, and make up DMEM containing 10% FBS to 8 mL/10 cm$^2$ dish, and observe the cells under microscope after 24 hours. Passage was performed with the degree of cell confluence greater than 80%;

(7) HEK293T/17 cells with good cell status and no pollution were selected, and each 2-6 petri dishes were used as a group. After trypsinizing the cells, 4-12 ml of complete medium was pipetted with an electric pipette to add 2 ml to each digested dish to avoid drying the dish; All cells were isolated into single cell suspensions using a 1 ml pipette and transferred to medium bottles;

(8) The remaining cells in the above 2-6 petri dishes were transferred to the medium bottles, and the petri dishes were rinsed with the medium again;

(9) Close the cap of the medium bottles and turn them upside down for about 10 times to fully mixed the cell suspension. Transfer the cells to 8-24 10 cm$^2$ petri dishes. The cell density of each dish shall be about $4 \times 10^6$ ↑/10 ml complete medium. In the case that the cell density was significantly different from the expected, the number of cells would be counted. Then the cells were inoculated according to the quantity of $4 \times 10^6$ per dish;

(10) Arrange each of the 6 petri dishes into a pile, and keep the fit between the upper and lower dishes. Shake the petri dishes left and right, back and forth several times to make cells fully spread out, and then put them into an incubator with 5% CO$_2$. The remaining cells were treated as the same;

(11) Upon Checking the passage cells, the cells shall be at 70-80% confluence, with full contour, good attachment and even distribution in petri dishes;

(12) For changing the solution, the medium was replaced with fresh complete medium with 9 ml per dish. The $CO_2$ concentration of incubator was increased to 8%;

(13) To prepare $DNA/CaCl_2$ according to N+0.5. The amount of HEK293T/17 cell transfection plasmid per dish was used in the following ratios: recombinant lentiviral plasmid (20 μg), pPac-GP (15 μg), pPac-R (10 μg), pEnv-G (7.5 μg). Take a new 5 ml centrifuge tube, add 0.5M CaCl2: 0.25 ml, recombinant lentiviral plasmid 20 μg: pPac-GP 15 μg: pPac-R 10 μg: pEnv-G 7.5 μg, supplement ultrapure water to 0.5 ml, and cover the cap to mix them fully;

(14) Take another 5 ml centrifuge tube and add 0.5 ml DNA/CaCl2 solution. Open a vortex mixer, hold the upper end of the 5 ml centrifuge tube with one hand, and make the bottom of the tube contact the oscillation chamber, so that the liquid could spread on the tube wall. Take a 1 ml pipette with anther hand to suck 0.5 mL 2×HBS solution, add it into the centrifuge tube slowly and control the flow velocity. It was advisable to complete the drip in half a minute. After 2×HBS was added, it should be oscillated for another 5 seconds, and then stop oscillating. It could be directly added into the cells that need transfection;

(15) Take a dish of cells and drop 1 mL calcium transfection solution in the centrifuge tube in the dish to distribute the calcium transfection solution throughout the petri dish as much as possible;

(16) After the calcium transfection solution was added, the petri dish was marked on the cover, and put back in another incubator with 5% $CO_2$. Make sure that the petri dish was placed horizontally, and that there were no more than 6 petri dishes in each pile. These dishes were placed in the incubator with 5% $CO_2$ for 6-8 h;

(17) The $CO_2$ concentration of the first incubator was adjusted at 5%;

(18) The cells status was check 24 hours later. The cell confluence should be around 80-85% and in good condition. Aspirate the medium and replace 10 ml of fresh DMEM complete medium;

(19) The transfection efficiency was observed 48 hours later. Most cells were still adherent. It could be seen that more than 95% of the cells would have green fluorescence. The supernatant of the same virus packaging was collected together, and 10 mL of fresh medium was added to the petri dish;

(20) The same virus supernatant was collected again 72 hours later. The two collections were put together, and the petri dishes were discarded; the supernatant collected at this time contained the recombinant lentiviral vector lvCAR19-1761~lvCAR19-1769.

Embodiment 2 Concentration and Detection of Recombinant Lentivirus Vector

I. Purification of Recombinant Lentiviral Vectors by Ion Exchange Chromatography (see FIG. 8);

(1) The collected supernatant was filtered through a 0.22 μm-0.8 μm PES filter using a Thermo vacuum pump to remove impurities;

(2) 1.5M NaCl 250 mM Tris-HCl (PH6-8) was added to the supernatant at a ratio of 1:1 to 1:10

(3) Two ion exchange columns were placed in series, and they were passed through sequentially by 4 ml 1M NaOH, 4 ml 1M NaCl, 5 ml 0.15M NaCl 25 mM Tris-HCl (pH 6-8) solution;

(4) The solution obtained in step 2 was pumped into the ion exchange column with a peristaltic pump at a rate of 1-10 ml/min;

(5) After all the supernatant was passed through the column, it was washed with 10 ml of 0.15M NaCl 25 mM Tris-HCl (pH 6-8) solution;

(6) According to the sample size, 1-5 ml of 1.5M NaCl 25 mM Tris-HCl (pH 6-8) was used for elution and the eluate was collected;

(7) The eluate was divided into tubes about 25 to 50 μl each, and stored in a refrigerator with −80° C. for long-term storage;

II. Titre Determination;

(1) 293T cells were inoculated with 24-well plates. The number of cells in each well was $5\times10^4$, and the volume of medium added was 500 ul. As the growth rate of different types of cells was different, the rate of cell fusion during viral infection was 40%-60%;

(2) Three sterile EP tubes were prepared, and 90 ul fresh complete medium (high glucose DMEM+10% FBS) was added into each tube to inoculate the cells. 24 hours later, the cells in the two pores were taken and counted with a hemocytometer to determine the actual number of cells at the time of infection, denoted as N;

(3) 10 ul of the virus stock to be determined was added to the first tube. After gently mixing, 10 ul of the virus stock was added to the second tube, and then sequentially operated until the last tube; 410 ul complete medium (high glucose DMEM+10% FBS) was added into each tube, and the final volume was 500 ul;

(4) 20 hours after the infection, the cultural supernatant was removed and changed into 500 μl complete medium (high glucose DMEM+10% FBS). The cells was continuously cultured for 48 hours in 5% $CO_2$;

(5) After 72 hours, the fluorescence expression was observed. Under normal circumstances, the number of fluorescence cells decreased with the increase of dilution ratio. At the same time, photos were taken;

(6) The cells were digested with 0.2 ml 0.25% trypsin-EDTA solution, and then they were placed at 37° C. for 1 minute. The whole cellular surface were purged with medium, and the cells were collected by centrifugation. Genomic DNA was extracted according to the instructions of DNeasy kit. 200 μl of eluent were added to each sample tube to remove DNA, and then they were quantified;

(7) The DNA detection qPCRmix manifold I was prepared (QPCR primer sequences were SEQ ID NO: 59 SEQ ID NO: 60):

TABLE 5

| | |
|---|---|
| 2× TaqMan Master Mix | 25 μl × n |
| Forward primer (100 pmol ml-1) | 0.1 μl × n |
| Reverse primer (100 pmol ml-1) | 0.1 μl × n |
| Probe (100 pmol ml-1) | 0.1 μl × n |
| $H_2O$ | 19.7 μl × n | n = number of reactions. For example, the total n were 40. 1 ml of 2× TaqMan Universal PCR Master Mix, 4 μl of forward primer, 4 μl of reverse primer, 4 μl of probe and 788 μl of $H_2O$ were mixed and Placed on ice after being shaken;

(8) The reference DNA detection qPCRmix manifold II were prepared (QPCR primer sequences were SEQ ID NO: 59 SEQ ID NO: 60):

TABLE 6

| 2× TaqMan Master Mix | 25 μl × n |
|---|---|
| 10 × RNaseP primer/probe mix | 2.5 μl × n |
| H₂O | 17.5 μl × n |

N = number of reactions. For example, the total n were 40. 1 ml of 2× TaqMan Universal PCR Master Mix, 100 μl pf 10 × RNaseP primer/probe mix and 700 μl of H₂O were mixed and placed on ice after being shaken;

(9) The PCR system was established on a pre-cooled 96-well PCR plate. Take 45 μl from each tube of manifold I to add to the wells of each row of A-D. Take 45 μl from each tube of manifold II to add to the wells of each row of E-G.

(10) 5 μl of the standard plasmid and the genomic DNA from the samples to be tested were taken respectively to add to the A-D row, and each sample was repeated once. 1 well was left to add 5 μl of water as no-template control.

(11) 5 μl of the genomic standards and the genomic DNA from the samples to be tested were taken respectively to add to the E-G row, and each sample was repeated once. 1 well was left to add 5 μl of water as no-template control.

(12) The quantitative PCR instrument used was the ABI PRISM 7500 quantitative system. The cyclic conditions were set to: 50° C. 2 min, 95° C. 10 min, (95° C. 15 sec, 60° C. 1 min)×40 cycle.

Data analysis: the copy number of lentiviral vectors integrated in the measured DNA samples was calibrated with the number of genomes to obtain the copy number of viruses integrated in each genome.

The calculation formula of integration units per ml (IU ml$^{-1}$) was as follows:

$$\text{IU ml}^{-1} = (C \times N \times D \times 1000)/V$$

TABLE 7

Of which:

C = the average virus copy number per genome integration
N = number of cells at the time of infection (approximately 1 × 10⁵)
D = dilution of the viral vector
V = the volume of diluted virus added

Figure 9:
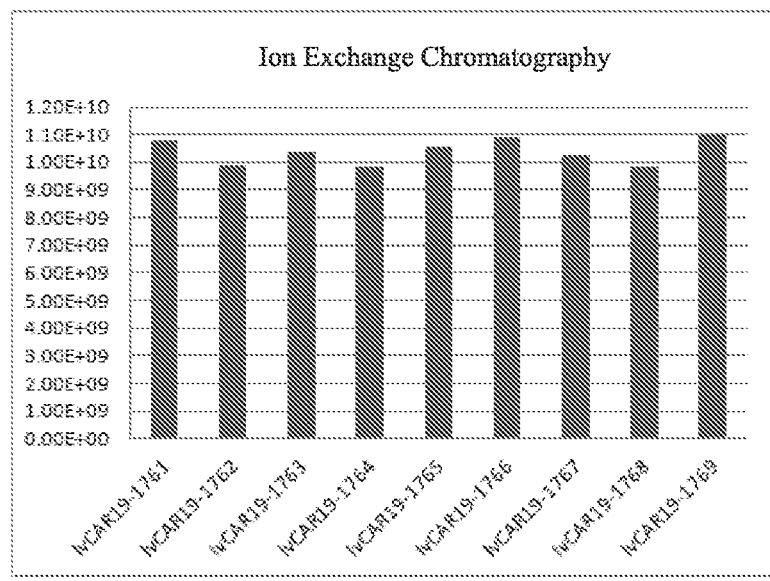
FIG. 9 shows the titer detection results of recombinant lentiviral vectors.

(13) Titer results of recombinant lentiviral vector lvCAR19-1761~lvCAR19-1769 (see FIG. 9);

III. Endotoxin Determination;

(1) The working standard of endotoxin was 15 EU per dose;

(2) Sensitivity of Tachypiens Amebocyte Lysate (TAL) λ=0.25 EU/ml, 0.5 ml/tube (3) Dilution of endotoxin standard: take one endotoxin standard, dilute it into 4λ, and 2λ, solution with BET water, seal with sealing film and vortex for 15 min; During dilution, each dilution step should be mixed on the vertex mixer for 30 s;

(4) Adding: Several TAL were taken, each was dissolved in 0.5 ml of BET water, and then divided into several exdotoxin-free tubes (0.1 ml each tube). Two of them were negative control which were added 0.1 ml of BET water to each of them;

Two tubes were positive control which were added 0.1 ml of endotoxin working standard solution with concentration of 2λ, to each of them;

Two tubes were positive control of sample which were added 0.1 ml sample solution contained 2λ, endotoxin standard (1 ml of 20× dilution of sample to be tested+1 ml of solution contained 4λ, endotoxin standard=2 ml of 40× dilution of sample contained 2λ, endotoxin standard).

0.1 ml of sample was added to the sample tube. The dilution ratio was in accordance with the Table 5. They were placed in water bath (or incubator) at 37±1° C. for 60±1 min;

TABLE 8

| Dilution Multiple | Original Fluid | 5 | 10 | 20 | 40 | 80 | 160 |
|---|---|---|---|---|---|---|---|
| Corresponding EU/ml | 0.25 | 1.25 | 2.5 | 5 | 10 | 20 | 40 |

Table 5 Dilution Ratio of Exdotoxin and Corresponding Endotoxin Content (5) The endotoxin detection results of the recombinant lentiviral vector lvCAR19-1761~lvCAR19-1769 (as shown in Table 6) showed that the endotoxin content was between 0-2.5 EU/ml, which met the requirements;

TABLE 9

| Dilution Multiple | Original Fluid | 5 | 10 | 20 | 40 | 80 | 160 |
|---|---|---|---|---|---|---|---|
| Corresponding EU/ml | 0.25 | 1.25 | 2.5 | 5 | 10 | 20 | 40 |
| lvCAR19-1761 | (+) | (+) | (−) | (−) | (−) | (−) | (−) |
| lvCAR19-1762 | (+) | (+) | (+) | (−) | (−) | (−) | (−) |
| lvCAR19-1763 | (+) | (+) | (−) | (−) | (−) | (−) | (−) |
| lvCAR19-1764 | (+) | (+) | (−) | (−) | (−) | (−) | (−) |
| lvCAR19-1765 | (−) | (−) | (−) | (−) | (−) | (−) | (−) |
| lvCAR19-1766 | (+) | (−) | (−) | (−) | (−) | (−) | (−) |
| lvCAR19-1767 | (+) | (+) | (−) | (−) | (−) | (−) | (−) |
| lvCAR19-1768 | (+) | (+) | (−) | (−) | (−) | (−) | (−) |
| lvCAR19-1769 | (+) | (+) | (+) | (−) | (−) | (−) | (−) |

Table 6 Detection Results of Endotoxin

IV. Determination and Comparison of *Mycoplasma*;

(1) Cell samples were cultured in antibiotic-free medium three days before the experiment;

(2) 1 ml of cell suspension was collected (the number of cells is greater than 1*10⁵) to place in a 1.5 ml centrifuge tube;

(3) Centrifuge at 13000×g for 1 min, collect the precipitate, and discard the medium;

(4) 500 ul of PBS was added. The mixture was blew and sucked with a pipette or vortex oscillated to resuspend the precipitate. Centrifuge at 13000×g for 5 min;

(5) To repeat step 4 once;

(6) 50 μl of Cell Lysis Buffer was added. The mixture was blew and sucked with a pipette. After fully mixed, it was incubated in the water at 55° C. for 20 min;

(7) The sample was heated at 95° C. for 5 min;

(8) After centrifugation at 13000×g for 5 min, 5 μl of supernatant was used as a template. 25 μl PCR reaction system was: 6.5 μl of ddH₂O, 1 μl of Myco Mix, 12.5 μl of 2× Taq Plus Mix Master (Dye Plus), 5 μl of template; PCR circulation condition was: 95° C. 30 sec, (95° C. 30 sec, 56° C. 30 sec, 72° C. 30 sec)*30 cycle, 72° C. 5 min.

Figure 10:
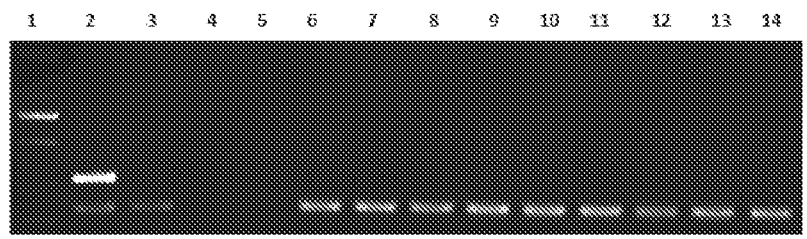
FIG. 10 shows the detection results of *mycoplasma* in different purification methods of recombinant lentiviral vectors. lane 1 is DL2000 marker, and the bands from top to bottom are: 2 kb, 1 kb, 750 bp, 500 bp, 250 bp, 100 bp; lane 2 is a positive control; lane 3 is a negative control; lane 4 is PBS; lane 5 is water; lane 6 is lvCAR19-1761; lane 7 is lvCAR19-1762; lane 8 is lvCAR19-1763; lane 9 is lvCAR19-1764; lane 10 is lvCAR19-1765; lane 11 is lvCAR19-1766; lane 12 is lvCAR19-1767; lane 13 is lvCAR19-1768; lane 14 is lvCAR19-1769.

(9) Detection results of *mycoplasma* (as shown in FIG. 10 and Table 7) showed that the recombinant lentiviral vector lvCAR19-1761~lvCAR19-1769 did not contain *mycoplasma*.

TABLE 10

| PCR template | PCR products | Determination description |
|---|---|---|
| Positive control | 280b and 150 bp were contained | Positive |
| | No band or only one band | Not positive |
| Negative control | 150bp band | Negative |
| | No band or more than two bands | Not negative |
| Sample | 280 and 150 bands were contained | Contaminated by mycoplasma |
| | Only 280 band | Severely contaminated by mycoplasma |
| | Only 150bp band | No mycoplasma contamination |
| | No band | Too few cells or PRC reaction was inhibited |

Table
Detection Results of *Mycoplasma*

Embodiment 3 Functional Detection of Recombinant Lentivrial Vector lvCAR19-1761~lvCAR19-1769

I. Detection of Cellular Level Expression of CAR Gene:

(1) After PBMC cells were infected with recombinant lentiviral vector lvCAR19-1761~lvCAR19-1769 and control virus MOCK, the cells were collected. RT-PCR was used to detect the transcription level of CAR mRNA and verify the expression of CAR gene. If the transcription level of CAR mRNA increased, it indicated that the transcription level of CAR gene was successfully expressed;

(2) After PBMC cells were infected with recombinant lentiviral vector lvCAR19-1761~lvCAR19-1769 and control virus MOCK, the cells were collected.

Western blot was used to detect the expression level of CAR protein and verify the expression of CAR gene. If the expression level of CAR protein increased, it indicated that the translation level of CAR gene was successfully expressed;

(3) lvCAR19-1761~lvCAR19-1769 with MOI=15 and control virus MOCK were infected with cells respectively. After 48 h, total RNA and total protein of the cells in the 6-well plate were extracted for fluorescence quantitative PCR and western blot assay. Specific steps: four wells of the 6-well plate were coated. Relevant PBS and RN were added to each well and overnight at 4° C. After 12 hours, the virus was coated according to MOI=15, and placed the plate in a incubator at 37° C. for 5 h; Take out the 6-well plate, and discard viral superatant. The plate was washed twice with PBS, coated with PBMC (isolated from human blood with lymphocyte separation solution) at $1*10^6$/well, and added 500 ul of medium (containing 10% serum, 20 U/ml IL-2, Polybrene Bug/ml). Then such plate was allowed to stand for 20 min, centrifuge at 1000 g for 20 min at 20° C., and culture for 48 h at 37° C.

(4) The total RNA of PBMC cells in 6-well plate was extracted by Trizol method, and the cDNA was amplified by reverse transcription. QPCR primers (SEQ ID NO: 63-SEQ ID NO: 64) were used for fluorescence quantitative PCR assay (the reaction system was shown in Table 8) to verify the transcription of its mRNA with Action as its control group.

TABLE 11

| Reagent | Volume (μl) |
|---|---|
| SYBR premix ex taq: | 10 μl |
| ROX Reverse Dye(50x) | 0.4 μl |
| Upstream primer (2.5 μM): | 0.5 μl |
| Downstream primer (2.5 μM): | 0.5 μl |
| cDNA | 1.0 μl |
| ddH$_2$O | 7.6 μl |

Table 8 20 μl qPCR Reaction System (5) Western Blot was used to separate the total protein extracted from PBMC by relative molecular weight by polyacrylamide gel electrophoresis. The protein was transferred to the PVDF membrane by wet transfer (4° C., 400 mA, 120 min). The PVDF membrane was blocked with a blocking solution (TB ST solution containing 5% skim milk) for 1 h at room temperature. The blocking solution was diluted with Biotinylated protein L at 1:1000, and then incubated with the blocked PVDF membrane at room temperature and overnight at 4° C. The membrane was washed three times with TBST, 10 min each time. The blocking solution was diluted with the corresponding SA-HRP at 1:500, and then used to incubated PVDF membrane at room temperature for 2 h. The membrane was washed three times with TBST, 10 min each time. ECL+Plus™ Western blotting system kit of Amersham was used for color development. X-ray optical development was used to obtain film showing bands.

Figure 11:
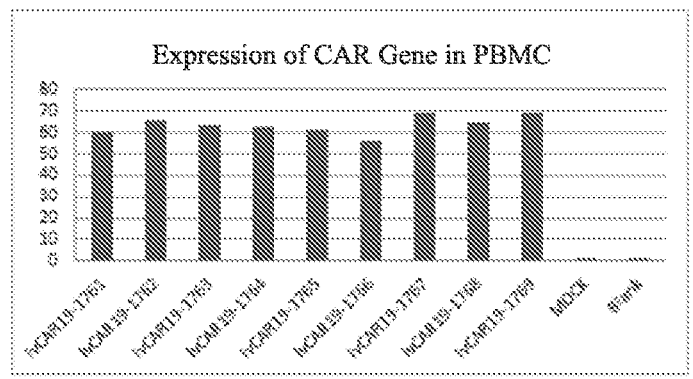
FIG. 11 is a bar chart of relative expression level of mRNA.

(6) RT-QPCR detection showed that the transcription level of CAR gene infected with PBMC by recombinant lentiviral vectors was significantly higher than that of control virus MOCK and blank cells (as shown in FIG. 11 and Table 9), indicating that the transcription level of CAR gene was successfully expressed.

TABLE 12

| Sample name | Actin (CT) | CAR (CT) | −ΔCt | −ΔΔCt | $2^{-\Delta\Delta Ct}$ |
|---|---|---|---|---|---|
| lvCAR19-1761 | 19.51814 | 29.58243 | −10.0643 | 5.91976 | 60.53753 |
| lvCAR19-1762 | 19.15714 | 29.11395 | −9.9568 | 6.02725 | 65.22033 |
| lvCAR19-1763 | 19.20232 | 29.19465 | −9.99233 | 5.99172 | 63.6338 |
| lvCAR19-1764 | 19.26301 | 29.27989 | −10.0169 | 5.96717 | 62.55993 |
| lvCAR19-1765 | 19.29964 | 19.35456 | −10.0549 | 5.92914 | 60.93236 |
| lvCAR19-1766 | 19.3805 | 29.55666 | −10.1762 | 5.8079 | 56.02099 |
| lvCAR19-1767 | 19.52714 | 29.39926 | −9.87212 | 6.11194 | 69.16335 |
| lvCAR19-1768 | 19.75401 | 29.71702 | −9.96295 | 6.02111 | 64.94329 |
| lvCAR19-1769 | 19.48712 | 29.36486 | −9.87774 | 6.10631 | 68.89426 |
| MOCK | 19.31164 | 35.11353 | −15.8019 | 0.18217 | 1.134585 |
| Blank | 19.94915 | 35.93321 | −15.9841 | 0 | 1 |

Table 9

Figure 12:
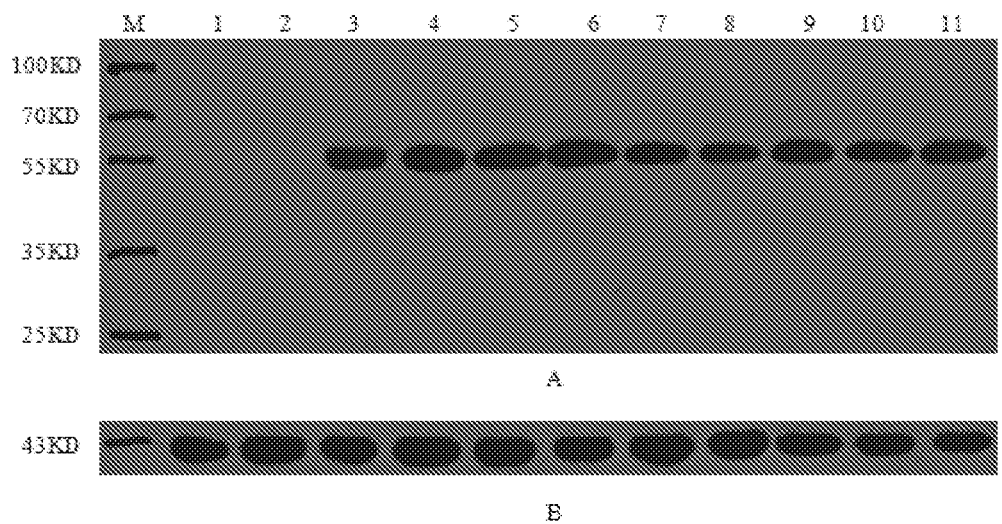
In FIG. 12 A, lane 1 is PBMC blank cells; lane 2 is the control virus MOCK; lane 3 is lvCAR19-1761; lane 4 is lvCAR19-1762; lane 5 is lvCAR19-1763; lane 6 is lvCAR19-1764; lane 7 is lvCAR19-1765; lane 8 is lvCAR19-1766; lane 9 is lvCAR19-1767; lane 10 is lvCAR19-1768; lane 11 is lvCAR19-1769.

(7) Western Blot results showed that the expression level of CAR protein infected with PBMC with recombinant lentiviral vectors was significantly higher than that of control virus MOCK and blank cells (as shown in FIG. 12), indicating that the translation level of CAR gene was successfully expressed.

II. Evaluation of IL-6 Know-Down Effect (mRNA Transcription Level and IL-6 Expression Level in Supernatant)

(1) CD19+K562 cells and PBMC cells were cultured separately;

(2) Four days before start of the experiment, the virus of lvCAR19-1761~lvCAR19-1769 with MOI=15 was infected with PBMC cells, and cultured for 72-96 h;

(3) $4 \times 10^5$ of target cells (CD19+K562) and $2.8 \times 10^6$ of effector cells (lvCAR19-1761-PBMC~lvCAR19-1769-PBMC cells) were collected, centrifuged at 800 g for 6 min, and supernatant was discarded;

(4) The target cells and effector cells were resuspended with 1 ml of 1×PBS solution respectively, centrifuged at 800 g for 6 min, and the supernatant was discarded;

(5) Step 4 was repeated once;

(6) Effector cells were resuspended with 700 ul medium (1640 medium+10% FBS), and target cells were resuspended with 2 ml medium (1640 medium +10% FBS).

(7) The experimental ports was set with the ratio of effector cells to target cells of 10:1, and the control group was set;

(8) Being plate centrifuged at 250×g for 5 min;

(9) They were co-cultured in a incubator with 5% $CO_2$ at 37° C. for 4 hours. 100 ul of co-cultured supernatant was collected to perform CBA for detecting the content of IL-6;

(10) They were continued to co-cultured in a incubator with 5% $CO_2$ at 37° C. for up to 24 hours. After being plate centrifuged at 1000×g for 2 min, 100 ul of co-cultured supernatant was collected to perform CBA for detecting the content of IL-6. Cells were collected to detect the transcription level of IL-6 mRNA;

(11) The steps of detecting IL-6 content by CBA was: IL-6 standard tube, sample tube and negative control tube were added 50 ul IL-6 trapping microparticles suspension respectively, and the microparticles were mixed before adding; 50 ul PE signal antibody was added to each tube; IL-6 standard tube was added with IL-6 standard diluent; The diluted sample and negative control solution were added into the sample tube and negative control tube respectively; They were incubated at room temperature keeping out of the sun for 3 h; Each tube was added with 1 ml of cleaning solution, and centrifuged at 200×g for 5 min; The supernatant was discarded; Each tube was added with 300 ul of cleaning solution to resuspend the microparticles; Attune® NxT flow cytometry was used to analyze these samples which were mixed fully for 3-5 s before starting the machine on that day;

(12) The total RNA of the mixed cells above was extracted by Trizol method, and the cDNA was amplified by reverse transcription. QPCR primers (SEQ ID NO: 65-SEQ ID NO: 66) were used for fluorescence quantitative PCR assay (the reaction system was shown in Table 6) to verify the transcription of its mRNA with Action as its control group.

Figure 13A:
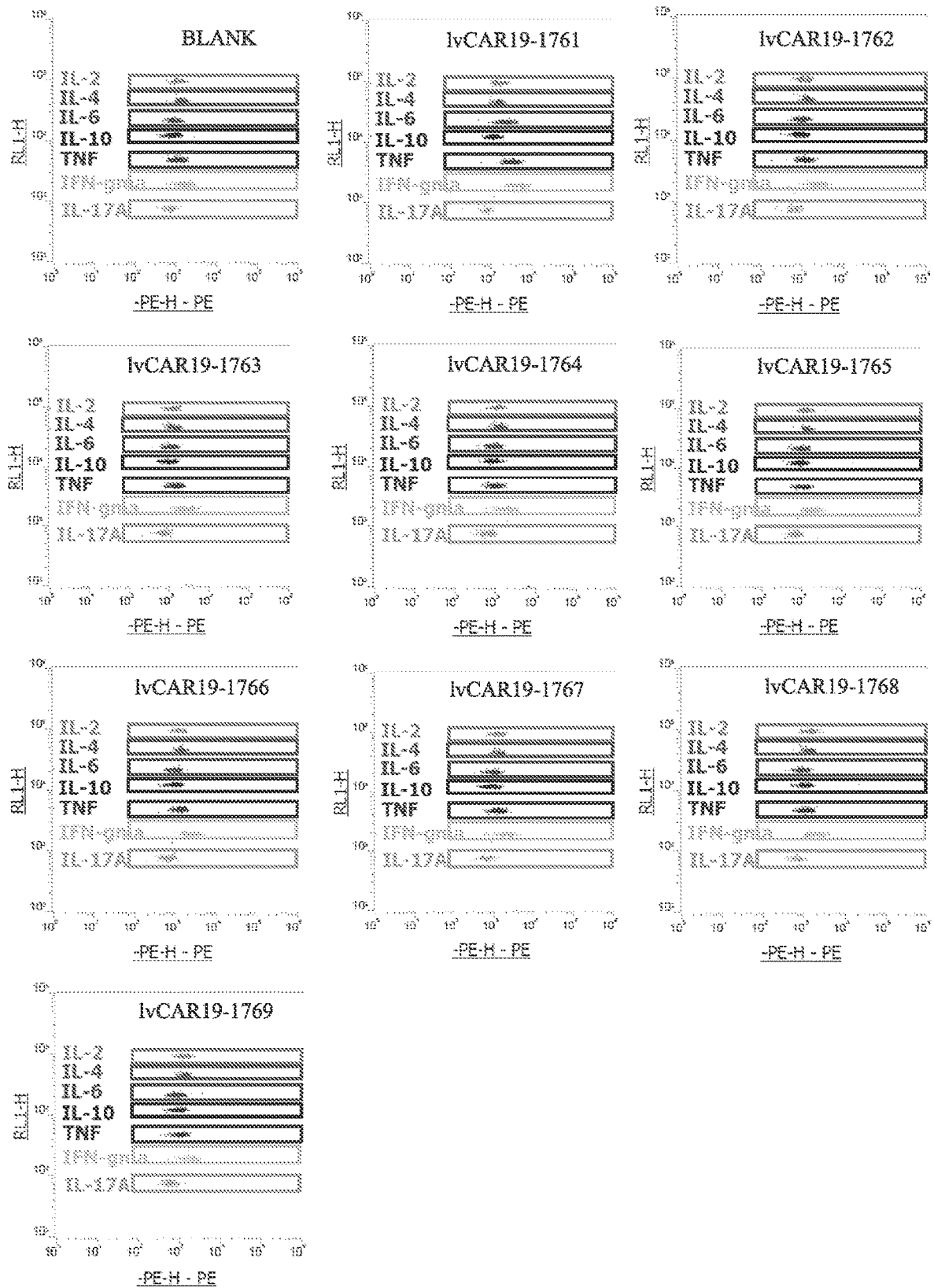
FIGS. 13A and 13B show the results of CBA detection in supernatants of IL-6 know-down recombinant lentivirus lvCAR19-1761~lvCAR19-1769 after incubation with target cells at 4 h and 24 h.
Figure 13B:
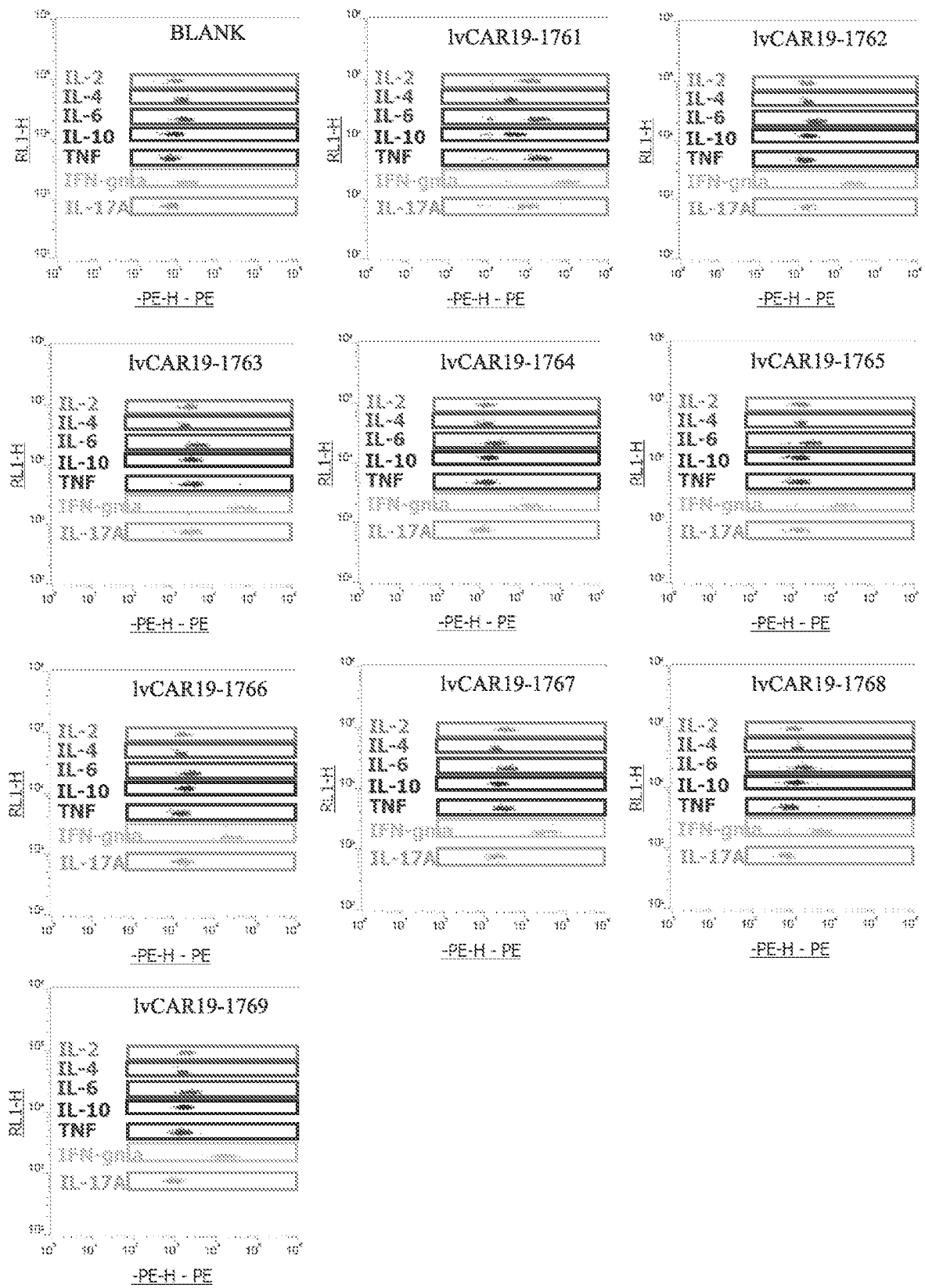
Figure 14:
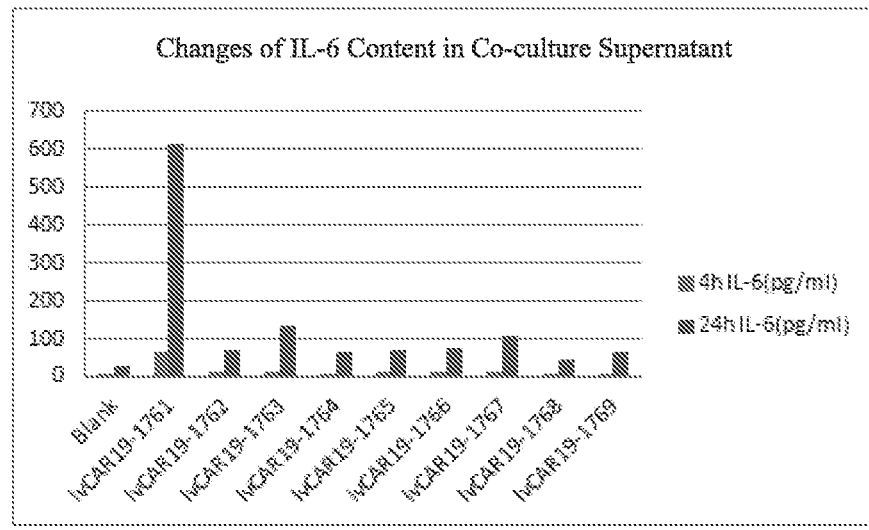
FIG. 14 shows the changes of IL-6 content in supernatants at 4 h and 24 h under different co-culture conditions of effector cells and target cells respectively.

(13) CBA detection results at 4 h and 2 h (as shown in FIG. 13) showed that after IL-6 know-down recombinant lentiviral vector was infected with PBMC and incubated with target cells, the supernatant content of IL-6 gene was significantly lower than that of control virus lvCAR19-1761 and blank cells (as shown in FIG. 14), indicating that the expression level of IL-6 gene was obviously decreased.

Figure 15:
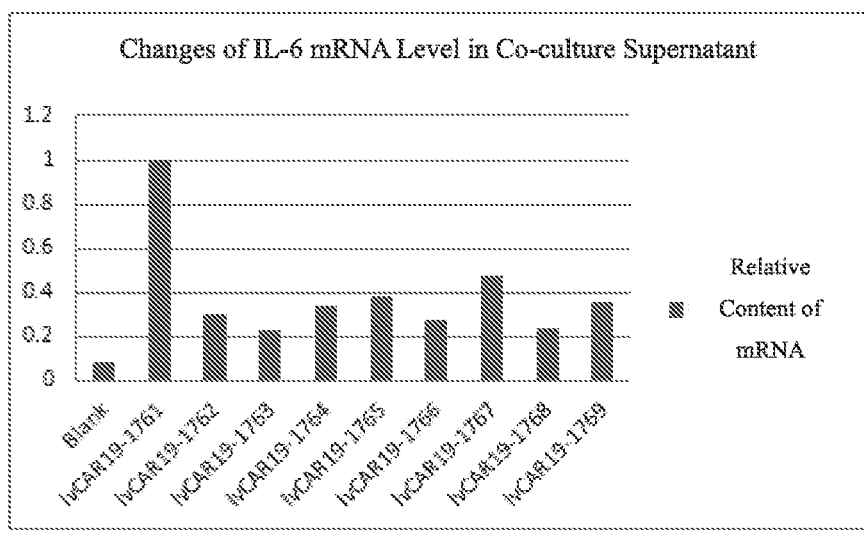
FIG. 15 shows the changes of mRNA transcription level at 24 h under different co-culture conditions of effector cells and target cells respectively.

(14) RT-QPCR detection results showed that IL-6 know-down recombinant lentiviral vector was infected with PBMC and incubated with target cells, the mRNA content of IL-6 gene was significantly lower than that of control virus lvCAR19-1761 and blank cells (as shown in FIG. 15), indicating that the transcription level of IL-6 gene was obviously decreased.

III. Effect Evaluation of Cell Killing Test (1) CD19+K562 cells and PBMC cells were cultured separately;

(2) Four days before start of the experiment, the virus of lvCAR19-1761~lvCAR19-1769 with MOI=15 was infected with PBMC cells, and cultured for 72-96 h;

(3) $4 \times 10^5$ of target cells (CD19+K562) and $2.8 \times 10^6$ of effector cells (CART cells) were collected, centrifuged at 800 g for 6 min, and supernatant was discarded;

(4) The target cells and effector cells were resuspended with 1 ml of 1×PBS solution respectively, centrifuged at 800 g for 6 min, and the supernatant was discarded;

(5) Step 3 was repeated once;

(6) Effector cells were resuspended with 700 ul medium (1640 medium+10% FBS), and target cells were resuspended with 2 ml medium (1640 medium +10% FBS);

(7) The experimental ports was set with the ratio of effector cells to target cells of 1:1, 5:1, 10:1, and the control group was set with 3 multiple wells each group;

(8) Being plate centrifuged at 250×g for 5 min;

(9) They were co-cultured in a incubator with 5% $CO_2$ at 37° C. for 4 hours;

(10) Being plate centrifuged at 250×g for 5 min;

(11) 50 ul of supernatant taken from each well was added into a new 96-well plate with 50 ul of substrate solution each well (light protection operation);

(12) They were incubated in the dark for 25 min;

(13) 50 ul of TMAH was added to each well;

(14) 490 nm absorbance was detected by enzyme-labeled instrument;

(15) Average of the three multiple wells was taken; The average of median background absorbance was subtracted from the absorbance of all experimental ports, target cell wells and effector cell wells; The average of control absorbance of volume correction was subtracted from the maximum absorbance of target cells.

Figure 16:
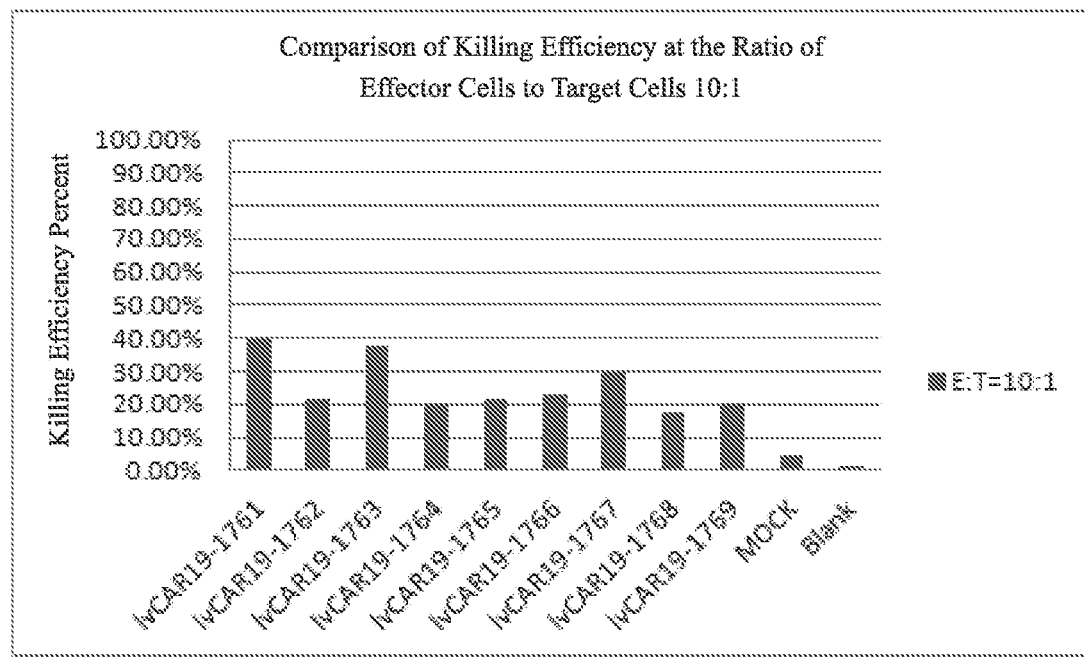
FIG. 16 shows the killing of target cells at 24 h after co-culture of different effector cells and target cells at a ratio of 10:1. E is the effector cell, and T is the target cell.

(16) The corrected values obtained in step 15 were taken into the following formula to calculate the percentage of cytotoxicity produced by each ratio of effector cells to target cells. Results as shown in FIG. 16, the killing efficiency of IL-6 know-down recombinant lentiviral vector transduced PBMC cells was significantly higher than that of PBMC blank cells at the ratio of effector cells to target cells 10:1, and lower than that of control virus lvCAR19-1761 transduced PBMC cells; wherein, the killing efficiency of lvCAR19-1763-PBMC was slightly lower than that of the control virus lvCAR19-1761-PBMC, however, the expression level of IL-6 decreased by more than 70%. In the future, less IL-6 could be released while killing tumor cells and effectively alleviating CRS.

Killing efficiency=(experimental ports–effector cell wells–target cell wells)/(target cell maximum well–target wells)×100%.

The better embodiments of the invention have been specified above, but the invention is not limited to the said embodiments. Technical personnel familiar with the field, without violating the spirit of the invention, make a variety of equivalent variations or substitutions, which are all included in the scope of the claim of this application.

IL-6 know-down siRNA expression cassette and its siRNA expression products described in the invention not only can be used in CAR19-T treatment of acute B lymphocytic leukemia (ALL) to eliminate or alleviate the symptoms of CRS, but also can be used to relieve CRS symptoms caused by CAR-T treatment for all types of tumors such as B-lymphoma, pancreatic cancer, brain glioma, bone cancer, even can be used to relieve CRS caused by other types of therapy.

The invention claimed is:

1. A pair of siRNAs of human IL-6, wherein, the siRNAs have nucleotide sequences selected from the group consisting of
   a. SEQ ID NO: 43 and SEQ ID NO: 44;
   b. SEQ ID NO: 45 and SEQ ID NO: 46;
   c. SEQ ID NO: 47 and SEQ ID NO: 48;
   d. SEQ ID NO: 49 and SEQ ID NO: 50;
   e. SEQ ID NO: 51 and SEQ ID NO: 52;
   f. SEQ ID NO: 53 and SEQ ID NO: 54;
   g. SEQ. ID NO: 55 and SEQ ID NO: 56; and
   h. SEQ ID NO: 57 and SEQ ID NO: 58.

2. A pharmaceutical preparation comprising the pair of siRNAs according to claim 1.

3. A recombinant expression vector comprising the siRNAs of claim 1.

4. The recombinant expression vector according to claim 3, wherein, the recombinant expression vector is a lentiviral expression vector, a retroviral expression vector, an adenovirus expression vector, an adeno-associated virus expression vector or a plasmid.

5. The recombinant expression vector according to claim 4, wherein, the recombinant expression vector is the lentiviral expression vector and the lentiviral expression vector comprises a prokaryotic replicon pUC Ori sequence used for plasmid replication, as shown in SEQ ID NO: 2; an AmpR sequence with Ampicillin resistance gene and used for a massive proliferation of target strains, as shown in SEQ ID NO: 1; a virus-replicon SV40 Ori sequence used for enhancing replication in eukaryocyte, as shown in SEQ ID NO: 3; a lentivirus packaging cis element used for lentivirus packaging; a ZsGreen1 green fluorescent protein used for eukaryocyte expressing green fluorescence, as shown in SEQ ID NO: 11; an IRES ribosome binding sequence used for the common transcription and expression of protein, as shown in SEQ ID NO: 12; a human EF1α promoter used for the eukaryotic transcription of chimeric antigen receptor genes, as shown in SEQ ID NO: 14; encoding gene of anti-CD19 chimeric antigen receptor used for making up a second or a third generation CAR integrating identification, transmission and promotion, as shown in SEQ ID NO: 52 or SEQ ID NO: 53; an enhanced woodchuck hepatitis virus post-transcriptional regulatory element (eWPRE) used for enhancing transgene expression efficiency, as shown in SEQ ID NO: 13; a human RNA polymerase III promoter hU6 used for intracellular transcription of the siRNAs, as shown in SEQ ID NO: 14.

6. The recombinant expression vector according to claim 5, wherein, the lentivirus packaging cis element comprises a lentivirus 5 terminal LTR as shown in SEQ ID NO: 5, a lentivirus 3 terminal Self-Inactivating LTR as shown in SEQ ID NO: 6, a Gag cis element as shown in SEQ ID NO: 7, an RRE cis element as shown in SEQ ID NO: 8, an env cis element as shown in SEQ ID NO: 9, and a cPPT cis element as shown in SEQ ID NO: 10.

7. The recombinant expression vector according to claim 5, wherein, the lentivirus packaging cis element comprises a lentivirus 5 terminal LTR as shown in SEQ ID NO: 5, a lentivirus 3 terminal Self-Inactivating LTR as shown in SEQ ID NO: 6, a Gag cis element as shown in SEQ ID NO: 7, an RRE cis element as shown in SEQ ID NO: 8, an env cis element as shown in SEQ ID NO: 9, a cPPT cis element as shown in SEQ ID NO: 10, and an RSV promoter as shown in SEQ ID NO: 4.

8. The recombinant expression vector according to claim 5, wherein, the eWPRE has 6 enhanced nucleotide mutations, including g.396G>A, g.397C>T, g.398T>C, g.399G>A, g.400A>T, and g.411A>T.

9. The recombinant expression vector according to claim 5, wherein, the anti-CD19 chimeric antigen receptor comprises SEQ ID NO: 52.

10. The recombinant expression vector according to claim 5, wherein, the anti-CD19 chimeric antigen receptor comprises SEQ ID NO: 53.

11. A method for constructing the recombinant expression vector of claim 3, the method comprising:
   (1) storing in a lentiviral skeleton plasmid pLenti-3G silencer the AmpR sequence with Ampicillin resistance gene of SEQ ID NO: 1, prokaryotic replicon pUC Ori sequence of SEQ ID NO: 2, virus-replicon SV40 Ori sequence of SEQ ID NO: 3, lentivirus packaging cis element used for lentivirus packaging, ZsGreen1 green fluorescent protein of SEQ ID NO: 11, IRES ribosome binding sequence of SEQ ID NO: 12, enhanced woodchuck hepatitis virus post-transcriptional regulatory element (eWPRE) of SEQ ID NO: 13, and human RNA polymerase III promoter hU6 of SEQ ID NO: 14;
   (2) combining the human EF1α promoter of SEQ ID NO: 15 and anti-CD19 chimeric antigen receptors used for making up a second or third generation CAR integrating identification, transmission and promotion into, and cloning into lentiviral skeleton plasmid through enzyme digestion, ligation and recombination reactions, the design scheme for the second or third generation CAR, to get the recombinant lentiviral plasmid designed with the second or third generation CAR;

(3) cloning into the recombinant lentiviral plasmid got through the step (2) the siRNAs and the negative control sequence as shown in SEQ ID NO: 41 and SEQ ID NO: 42 to get IL-6 knock-down recombinant lentiviral plasmids;

(4) transfecting recombinant lentiviral plasmids (pCAR19-1761~pCAR19-1769) got through the step (3) together with lentiviral packaging plasmids pPac-GP and pPac-R and membrane protein plasmid pEnv-G, respectively into HEK293T/17 cell, and collecting supernate containing recombinant lentiviral vectors, to be released into cell culture supernate after packaging successfully and after gene transcript expression in HEK293T/17 cell; and (5) getting recombinant lentiviral vectors by purifying recombinant lentivirus supernatant got through the step (4) with Ion exchange modes of extraction filtration, adsorption, and elution.

12. The method of claim 11, wherein, in the step (4), through the extraction filtration, a volume of the supernatant is controlled at 200 ml-2000 ml, and a vacuum degree of the supernatant at −0.5 MPA--0.9 MPA, to prevent loss of vector caused by plugging holes; through the said extraction filtration adsorption, the PH of solution is controlled at 6-8 to prevent inactivation of vector resulting from changes in PH; through the said elution, an ionic strength of eluant is controlled at 0.5M-1.0M to prevent incomplete elution or inactivation of vector arising out of changes in the ionic strength.

13. A pharmaceutical preparation comprising the recombinant expression vector according to claim 3.

14. A CART cell, wherein, the CART cell is a T lymphocyte modified by the siRNAs of claim 1.

15. A pharmaceutical preparation comprising the CART cell according to claim 14.

16. A pharmaceutical preparation comprising the recombinant expression vector according to claim 4.

17. A pharmaceutical preparation comprising the recombinant expression vector according to claim 5.

18. A pharmaceutical preparation comprising the recombinant expression vector according to claim 6.

19. A pharmaceutical preparation comprising the recombinant expression vector according to claim 7.

20. A pharmaceutical preparation comprising the recombinant expression vector according to claim 8.

* * * * *

SEQUENCE LISTING

<160> NUMBER OF SEQ ID NOS: 66

<210> SEQ ID NO 1
<211> LENGTH: 861
<212> TYPE: DNA
<213> ORGANISM: Artificial sequence
<220> FEATURE:
<223> OTHER INFORMATION: the sequence is synthetized.

<400> SEQUENCE: 1

```
atgagtattc aacatttccg tgtcgccctt attcccttttt ttgcggcatt ttgccttcct      60
gttttttgctc acccagaaac gctggtgaaa gtaaaagatg ctgaagatca gttgggtgca     120
cgagtgggtt acatcgaact ggatctcaac agcggtaaga tccttgagag ttttcgcccc     180
gaagaacgtt ttccaatgat gagcactttt aaagttctgc tatgtggcgc ggtattatcc     240
cgtattgacg ccgggcaaga gcaactcggt cgccgcatac actattctca gaatgacttg     300
gttgagtact caccagtcac agaaaagcat cttacggatg gcatgacagt aagagaatta     360
tgcagtgctg ccataaccat gagtgataac actgcggcca acttacttct gacaacgatc     420
ggaggaccga aggagctaac cgcttttttg cacaacatgg gggatcatgt aactcgcctt     480
gatcgttggg aaccggagct gaatgaagcc ataccaaacg acgagcgtga ccaccgatg     540
cctgtagcaa tggcaacaac gttgcgcaaa ctattaactg gcgaactact tactctagct     600
tcccggcaac aattaataga ctggatggag gcggataaag ttgcaggacc acttctgcgc     660
tcggcccttc cggctggctg gtttattgct gataaatctg gagccggtga gcgtgggtct     720
cgcggtatca ttgcagcact ggggccagat ggtaagccct cccgtatcgt agttatctac     780
acgacgggga gtcaggcaac tatgatgaa cgaaatagac agatcgctga gataggtgcc     840
tcactgatta agcattggta a                                               861
```

<210> SEQ ID NO 2
<211> LENGTH: 674
<212> TYPE: DNA
<213> ORGANISM: Artificial sequence
<220> FEATURE:
<223> OTHER INFORMATION: the sequence is synthetized.

<400> SEQUENCE: 2

```
cccgtagaaa agatcaaagg atcttcttga gatccttttt ttctgcgcgt aatctgctgc      60
ttgcaaacaa aaaaccacc gctaccagcg gtggtttgtt tgccggatca agagctacca     120
actctttttc cgaaggtaac tggcttcagc agagcgcaga taccaaatac tgtccttcta     180
gtgtagccgt agttaggcca ccacttcaag aactctgtag caccgcctac atacctcgct     240
ctgctaatcc tgttaccagt ggctgctgcc agtggcgata gtcgtgtct taccgggttg     300
gactcaagac gatagttacc ggataaggcg cagcggtcgg gctgaacggg gggttcgtgc     360
acacagccca gcttggagcg aacgacctac accgaactga gatacctaca gcgtgagcta     420
tgagaaagcg ccacgcttcc cgaagggaga aaggcggaca ggtatccggt aagcggcagg     480
gtcggaacag gagagcgcac gagggagctt ccaggggga acgcctggta tctttatagt     540
cctgtcgggt ttcgccacct ctgacttgag cgtcgatttt tgtgatgctc gtcaggggg     600
cggagcctat ggaaaaacgc cagcaacgcg gcctttttac ggttcctggc cttttgctgg     660
cctttttgctc acat                                                      674
```

<210> SEQ ID NO 3
<211> LENGTH: 147

<212> TYPE: DNA
<213> ORGANISM: Artificial sequence
<220> FEATURE:
<223> OTHER INFORMATION: the sequence is synthetized.

<400> SEQUENCE: 3

```
atcccgcccc taactccgcc cagttccgcc cattctccgc cccatggctg actaattttt      60
tttatttatg cagaggccga ggccgcctcg gcctctgagc tattccagaa gtagtgagga     120
ggcttttttg gaggcctaga cttttgc                                         147
```

<210> SEQ ID NO 4
<211> LENGTH: 228
<212> TYPE: DNA
<213> ORGANISM: Artificial sequence
<220> FEATURE:
<223> OTHER INFORMATION: the sequence is synthetized.

<400> SEQUENCE: 4

```
gtagtcttat gcaatactct tgtagtcttg caacatggta acgatgagtt agcaacatgc      60
cttacaagga gagaaaaagc accgtgcatg ccgattggtg gaagtaaggt ggtacgatcg     120
tgccttatta ggaaggcaac agacgggtct gacatggatt ggacgaacca ctgaattgcc     180
gcattgcaga gatattgtat ttaagtgcct agctcgatac aataaacg                  228
```

<210> SEQ ID NO 5
<211> LENGTH: 180
<212> TYPE: DNA
<213> ORGANISM: Artificial sequence
<220> FEATURE:
<223> OTHER INFORMATION: the sequence is synthetized.

<400> SEQUENCE: 5

```
ggtctctctg gttagaccag atctgagcct gggagctctc tggctaacta gggaacccac      60
tgcttaagcc tcaataaagc ttgccttgag tgcttcaagt agtgtgtgcc cgtctgttgt     120
gtgactctgg taactagaga tccctcagac ccttttagtc agtgtggaaa atctctagca     180
```

<210> SEQ ID NO 6
<211> LENGTH: 234
<212> TYPE: DNA
<213> ORGANISM: Artificial sequence
<220> FEATURE:
<223> OTHER INFORMATION: the sequence is synthetized.

<400> SEQUENCE: 6

```
tgctagagat tttccacact gactaaaagg gtctgaggga tctctagtta ccagagtcac      60
acaacagacg ggcacacact acttgaagca ctcaaggcaa gctttattga ggcttaagca     120
gtgggttccc tagttagcca gagagctccc aggctcagat ctggtctaac cagagagacc     180
cagtacaagc aaaaagcaga tcttattttc gttgggagtg aattagccct tcca            234
```

<210> SEQ ID NO 7
<211> LENGTH: 353
<212> TYPE: DNA
<213> ORGANISM: Artificial sequence
<220> FEATURE:
<223> OTHER INFORMATION: the sequence is synthetized.

<400> SEQUENCE: 7

```
atgggtgcga gagcgtcagt attaagcggg ggagaattag atcgcgatgg gaaaaaattc      60
ggttaaggcc agggggaaag aaaaaatata aattaaaaca tatagtatgg gcaagcaggg     120
```

-continued

```
agctagaacg attcgcagtt aatcctggcc tgttagaaac atcagaaggc tgtagacaaa        180
tactgggaca gctacaacca tcccttcaga caggatcaga agaacttaga tcattatata        240
atacagtagc aaccctctat tgtgtgcatc aaaggataga gataaagac  accaaggaag        300 ctttagacaa gatagaggaa gagcaaaaca aaagtaagac caccgcacag caa              353
```

<210> SEQ ID NO 8
<211> LENGTH: 233
<212> TYPE: DNA
<213> ORGANISM: Artificial sequence
<220> FEATURE:
<223> OTHER INFORMATION: the sequence is synthetized.

<400> SEQUENCE: 8

```
aggagctttg ttccttgggt tcttgggagc agcaggaagc actatgggcg cagcctcaat        60
gacgctgacg gtacaggcca gacaattatt gtctggtata gtgcagcagc agaacaattt       120
gctgagggct attgaggcgc aacagcatct gttgcaactc acagtctggg gcatcaagca       180
gctccaggca agaatcctgg ctgtggaaag atacctaaag gatcaacagc tcc              233
```

<210> SEQ ID NO 9
<211> LENGTH: 489
<212> TYPE: DNA
<213> ORGANISM: Artificial sequence
<220> FEATURE:
<223> OTHER INFORMATION: the sequence is synthetized.

<400> SEQUENCE: 9

```
tggggatttg gggttgctct ggaaaactca tttgcaccac tgctgtgcct tggaatgcta        60
gttggagtaa taaatctctg aacagattg  gaatcacacg acctggatgg agtgggacag       120
agaaattaac aattcacaa  gcttaataca ctccttaatt gaagaatcgc aaaaccagca       180
agaaaagaat gaacaagaat tattggaatt agataaatgg gcaagtttgt ggaattggtt       240
taacataaca aattggctgt ggtatataaa attattcata atgatagtag gaggcttggt       300
aggtttaaga atagttttg  ctgtactttc tatagtgaat agagttaggc agggatattc       360
accattatcg tttcagaccc acctcccaac cccgagggga cccgacaggc ccgaaggaat       420
agaagaagaa ggtggagaga gagacagaga cagatccatt cgattagtga acggatctcg       480
acggttaac                                                               489
```

<210> SEQ ID NO 10
<211> LENGTH: 119
<212> TYPE: DNA
<213> ORGANISM: Artificial sequence
<220> FEATURE:
<223> OTHER INFORMATION: the sequence is synthetized.

<400> SEQUENCE: 10

```
ttttaaaaga aaggggggga ttggggggta cagtgcaggg gaaagaatag tagacataat        60
agcaacagac atacaaacta agaattaca  aaaacaaatt acaaaaattc aaaatttta        119
```

<210> SEQ ID NO 11
<211> LENGTH: 696
<212> TYPE: DNA
<213> ORGANISM: Artificial sequence
<220> FEATURE:
<223> OTHER INFORMATION: the sequence is synthetized.

<400> SEQUENCE: 11

```
atggcccagt ccaagcacgg cctgaccaag gagatgacca tgaagtaccg catggagggc        60
```

```
tgcgtggacg gccacaagtt cgtgatcacc ggcgagggca tcggctaccc cttcaagggc    120
aagcaggcca tcaacctgtg cgtggtggag ggcggcccct tgcccttcgc cgaggacatc    180
ttgtccgccg ccttcatgta cggcaaccgc gtgttcaccg agtaccccca ggacatcgtc    240
gactacttca agaactcctg ccccgccggc tacacctggg accgctcctt cctgttcgag    300
gacggcgccg tgtgcatctg caacgccgac atcaccgtga gcgtggagga gaactgcatg    360
taccacgagt ccaagttcta cggcgtgaac ttccccgccg acggcccgt gatgaagaag     420 atgaccgaca actgggagcc ctcctgcgag aagatcatcc ccgtgcccaa gcagggcatc    480
ttgaagggcg acgtgagcat gtacctgctg ctgaaggacg tggccgcttt cgctgccag    540 ttcgacaccg tgtacaaggc caagtccgtg ccccgcaaga tgcccgactg cacttcatc    600 cagcacaagc tgacccgcga ggaccgcagc gacgccaaga accagaagtg gcacctgacc    660
gagcacgcca tcgcctccgg ctccgccttg ccctga                              696
```

<210> SEQ ID NO 12
<211> LENGTH: 575
<212> TYPE: DNA
<213> ORGANISM: Artificial sequence
<220> FEATURE:
<223> OTHER INFORMATION: the sequence is synthetized.

<400> SEQUENCE: 12

```
gcccctctcc ctccccccc cctaacgtta ctggccgaag ccgcttggaa taaggccggt      60
gtgcgtttgt ctatatgtta ttttccacca tattgccgtc ttttggcaat gtgagggccc    120
ggaaacctgg ccctgtcttc ttgacgagca ttcctagggg tctttcccct ctcgccaaag    180
gaatgcaagg tctgttgaat gtcgtgaagg aagcagttcc tctggaagct tcttgaagac    240
aaacaacgtc tgtagcgacc ctttgcaggc agcggaaccc cccacctggc gacaggtgcc    300
tctgcggcca aaagccacgt gtataagata cacctgcaaa ggcggcacaa ccccagtgcc    360
acgttgtgag ttggatagtt gtggaaagag tcaaatggct cacctcaagc gtattcaaca    420
aggggctgaa ggatgcccag aaggtacccc attgtatggg atctgatctg gggcctcggt    480
gcacatgctt tacatgtgtt tagtcgaggt taaaaaacgt ctaggccccc cgaaccacgg    540
ggacgtggtt ttcctttgaa aaacacgatg ataat                               575
```

<210> SEQ ID NO 13
<211> LENGTH: 592
<212> TYPE: DNA
<213> ORGANISM: Artificial sequence
<220> FEATURE:
<223> OTHER INFORMATION: the sequence is synthetized.

<400> SEQUENCE: 13

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
```

| | |
|---|---|
| aatccagcgg accttccttc ccgcggcctg ctgccggctc tgcggcctct tccgcgtctt | 540 |
| cgccttcgcc ctcagacgag tcggatctcc ctttgggccg cctccccgcc tg | 592 |

<210> SEQ ID NO 14
<211> LENGTH: 256
<212> TYPE: DNA
<213> ORGANISM: Artificial sequence
<220> FEATURE:
<223> OTHER INFORMATION: the sequence is synthetized.

<400> SEQUENCE: 14

| | |
|---|---|
| cccettcacc gagggcctat ttcccatgat tccttcatat ttgcatatac gatacaaggc | 60 |
| tgttagagag ataattggaa ttaatttgac tgtaaacaca aagatattag tacaaaatac | 120 |
| gtgacgtaga aagtaataat ttcttgggta gtttgcagtt ttaaaattat gttttaaaat | 180 |
| ggactatcat atgcttaccg taacttgaaa gtatttcgat ttcttggctt tatatatctt | 240 |
| gtggaaagga cgaaac | 256 |

<210> SEQ ID NO 15
<211> LENGTH: 1178
<212> TYPE: DNA
<213> ORGANISM: Artificial sequence
<220> FEATURE:
<223> OTHER INFORMATION: the sequence is synthetized.

<400> SEQUENCE: 15

| | |
|---|---|
| gctccggtgc ccgtcagtgg gcagagcgca catcgcccac agtccccgag aagttggggg | 60 |
| gaggggtcgg caattgaacc ggtgcctaga aaggtggcg cggggtaaac tgggaaagtg | 120 |
| atgtcgtgta ctggctccgc cttttttcccg agggtggggg agaaccgtat ataagtgcag | 180 |
| tagtcgccgt gaacgttctt tttcgcaacg ggtttgccgc cagaacacag gtaagtgccg | 240 |
| tgtgtggttc ccgcgggcct ggcctcttta cgggttatgg cccttgcgtg ccttgaatta | 300 |
| cttccacctg gctgcagtac gtgattcttg atcccgagct tcgggttgga agtgggtggg | 360 |
| agagttcgag gccttgcgct taaggagccc cttcgcctcg tgcttgagtt gaggcctggc | 420 |
| ctgggcgctg gggccgccgc gtgcgaatct ggtggcacct tcgcgcctgt ctcgctgctt | 480 |
| tcgataagtc tctagccatt taaaattttt gatgacctgc tgcgacgctt ttttctggc | 540 |
| aagatagtct tgtaaatgcg ggccaagatc tgcacactgg tatttcggtt tttggggccg | 600 |
| cgggcggcga cggggcccgt gcgtcccagc gcacatgttc ggcgaggcgg ggcctgcgag | 660 |
| cgcggccacc gagaatcgga cggggtagt ctcaagctgg ccggcctgct ctggtgcctg | 720 |
| gcctcgcgcc gccgtgtatc gccccgccct gggcggcaag gctggcccgg tcggcaccag | 780 |
| ttgcgtgagc ggaaagatgg ccgcttcccg gccctgctgc agggagctca aaatggagga | 840 |
| cgcggcgctc gggagagcgg gcgggtgagt cacccacaca aaggaaaagg gcctttccgt | 900 |
| cctcagccgt cgcttcatgt gactccactg agtaccgggc gccgtccagg cacctcgatt | 960 |
| agttctcgag cttttggagt acgtcgtctt taggttgggg ggagggggttt tatgcgatgg | 1020 |
| agtttccccca cactgagtgg gtggagactg aagttaggcc agcttggcac ttgatgtaat | 1080 |
| tctccttgga atttgccctt tttgagtttg gatcttggtt cattctcaag cctcagacag | 1140 |
| tggttcaaag ttttttttctt ccatttcagg tgtcgtga | 1178 |

<210> SEQ ID NO 16
<211> LENGTH: 63
<212> TYPE: DNA
<213> ORGANISM: Artificial sequence

```
<220> FEATURE:
<223> OTHER INFORMATION: the sequence is synthetized.

<400> SEQUENCE: 16
atggccttac cagtgaccgc cttgctcctg ccgctggcct tgctgctcca cgccgccagg    60
ccg                                                                  63

<210> SEQ ID NO 17
<211> LENGTH: 321
<212> TYPE: DNA
<213> ORGANISM: Artificial sequence
<220> FEATURE:
<223> OTHER INFORMATION: the sequence is synthetized.

<400> SEQUENCE: 17
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat tacactcagg agtcccatca   180
aggttcagtg gcagtgggtc tggaacagat tattctctca ccattagcaa cctggagcaa   240
gaagatattg ccacttactt ttgccaacag ggtaatacgc ttccgtacac gttcggaggg   300
gggaccaagc tggagatcac a                                              321

<210> SEQ ID NO 18
<211> LENGTH: 45
<212> TYPE: DNA
<213> ORGANISM: Artificial sequence
<220> FEATURE:
<223> OTHER INFORMATION: the sequence is synthetized.

<400> SEQUENCE: 18
ggtggcggtg gctcgggcgg tggtgggtcg ggtggcggcg gatct                    45

<210> SEQ ID NO 19
<211> LENGTH: 360
<212> TYPE: DNA
<213> ORGANISM: Artificial sequence
<220> FEATURE:
<223> OTHER INFORMATION: the sequence is synthetized.

<400> SEQUENCE: 19
gaggtgaaac tgcaggagtc aggacctggc ctggtggcgc cctcacagag cctgtccgtc    60
acatgcactg tctcaggggt ctcattaccc gactatggtg taagctggat tcgccagcct   120
ccacgaaagg gtctggagtg gctgggagta atatggggta gtgaaaccac atactataat   180
tcagctctca aatccagact gaccatcatc aaggacaact ccaagagcca agttttctta   240
aaaatgaaca gtctgcaaac tgatgacaca gccatttact actgtgccaa acattattac   300
tacggtggta gctatgctat ggactactgg ggccaaggaa cctcagtcac cgtctcctca   360

<210> SEQ ID NO 20
<211> LENGTH: 141
<212> TYPE: DNA
<213> ORGANISM: Artificial sequence
<220> FEATURE:
<223> OTHER INFORMATION: the sequence is synthetized.

<400> SEQUENCE: 20
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
```

```
gacttcgcct gtgatatcta c                                              141
```

<210> SEQ ID NO 21
<211> LENGTH: 66
<212> TYPE: DNA
<213> ORGANISM: Artificial sequence
<220> FEATURE:
<223> OTHER INFORMATION: the sequence is synthetized.

<400> SEQUENCE: 21

```
atctgggcgc ccttggccgg gacttgtggg gtccttctcc tgtcactggt tatcacccttt   60 tactgc                                                               66
```

<210> SEQ ID NO 22
<211> LENGTH: 126
<212> TYPE: DNA
<213> ORGANISM: Artificial sequence
<220> FEATURE:
<223> OTHER INFORMATION: the sequence is synthetized.

<400> SEQUENCE: 22

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

<210> SEQ ID NO 23
<211> LENGTH: 336
<212> TYPE: DNA
<213> ORGANISM: Artificial sequence
<220> FEATURE:
<223> OTHER INFORMATION: the sequence is synthetized.

<400> SEQUENCE: 23

```
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336
```

<210> SEQ ID NO 24
<211> LENGTH: 123
<212> TYPE: DNA
<213> ORGANISM: Artificial sequence
<220> FEATURE:
<223> OTHER INFORMATION: the sequence is synthetized.

<400> SEQUENCE: 24

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123
```

<210> SEQ ID NO 25
<211> LENGTH: 36
<212> TYPE: DNA
<213> ORGANISM: Artificial sequence
<220> FEATURE:
<223> OTHER INFORMATION: the sequence is synthetized.

<400> SEQUENCE: 25

```
attcaaaatt ttatcgatgc tccggtgccc gtcagt                              36
```

<210> SEQ ID NO 26
<211> LENGTH: 22
<212> TYPE: DNA
<213> ORGANISM: Artificial sequence
<220> FEATURE:
<223> OTHER INFORMATION: the sequence is synthetized.

<400> SEQUENCE: 26

```
tcacgacacc tgaaatggaa ga                                            22
```

<210> SEQ ID NO 27
<211> LENGTH: 42
<212> TYPE: DNA
<213> ORGANISM: Artificial sequence
<220> FEATURE:
<223> OTHER INFORMATION: the sequence is synthetized.

<400> SEQUENCE: 27

```
ggtgtcgtga ggatccgcca ccatggcctt accagtgacc gc                      42
```

<210> SEQ ID NO 28
<211> LENGTH: 31
<212> TYPE: DNA
<213> ORGANISM: Artificial sequence
<220> FEATURE:
<223> OTHER INFORMATION: the sequence is synthetized.

<400> SEQUENCE: 28

```
gtgtcatctg gatgtccggc ctggcggcgt g                                  31
```

<210> SEQ ID NO 29
<211> LENGTH: 41
<212> TYPE: DNA
<213> ORGANISM: Artificial sequence
<220> FEATURE:
<223> OTHER INFORMATION: the sequence is synthetized.

<400> SEQUENCE: 29

```
cacgccgcca ggccggacat ccagatgaca cagactacat c                       41
```

<210> SEQ ID NO 30
<211> LENGTH: 20
<212> TYPE: DNA
<213> ORGANISM: Artificial sequence
<220> FEATURE:
<223> OTHER INFORMATION: the sequence is synthetized.

<400> SEQUENCE: 30

```
tgtgatctcc agcttggtcc                                               20
```

<210> SEQ ID NO 31
<211> LENGTH: 82
<212> TYPE: DNA
<213> ORGANISM: Artificial sequence
<220> FEATURE:
<223> OTHER INFORMATION: the sequence is synthetized.

<400> SEQUENCE: 31

```
caagctggag atcacaggtg gcggtggctc gggcggtggt gggtcgggtg gcggcggatc   60
tgaggtgaaa ctgcaggagt ca                                            82
```

<210> SEQ ID NO 32

```
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 32
tgaggagacg gtgactgagg t                                              21

<210> SEQ ID NO 33
<211> LENGTH: 33
<212> TYPE: DNA
<213> ORGANISM: Artificial sequence
<220> FEATURE:
<223> OTHER INFORMATION: the sequence is synthetized.

<400> SEQUENCE: 33
agtcaccgtc tcctcaacca cgacgccagc gcc                                 33

<210> SEQ ID NO 34
<211> LENGTH: 23
<212> TYPE: DNA
<213> ORGANISM: Artificial sequence
<220> FEATURE:
<223> OTHER INFORMATION: the sequence is synthetized.

<400> SEQUENCE: 34
gtagatatca caggcgaagt cca                                            23

<210> SEQ ID NO 35
<211> LENGTH: 33
<212> TYPE: DNA
<213> ORGANISM: Artificial sequence
<220> FEATURE:
<223> OTHER INFORMATION: the sequence is synthetized.

<400> SEQUENCE: 35
cgcctgtgat atctacatct gggcgcccct ggc                                 33

<210> SEQ ID NO 36
<211> LENGTH: 39
<212> TYPE: DNA
<213> ORGANISM: Artificial sequence
<220> FEATURE:
<223> OTHER INFORMATION: the sequence is synthetized.

<400> SEQUENCE: 36
tctttctgcc ccgtttgcag taaagggtga taaccagtg                           39

<210> SEQ ID NO 37
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 37
aaacggggca gaaagaaact c                                              21

<210> SEQ ID NO 38
<211> LENGTH: 40
<212> TYPE: DNA
<213> ORGANISM: Artificial sequence
<220> FEATURE:
<223> OTHER INFORMATION: the sequence is synthetized.

<400> SEQUENCE: 38
```
tgctgaactt cactctcagt tcacatcctc cttcttcttc                         40

<210> SEQ ID NO 39
<211> LENGTH: 22
<212> TYPE: DNA
<213> ORGANISM: Artificial sequence
<220> FEATURE:
<223> OTHER INFORMATION: the sequence is synthetized.

<400> SEQUENCE: 39
agagtgaagt tcagcaggag cg                                            22

<210> SEQ ID NO 40
<211> LENGTH: 34
<212> TYPE: DNA
<213> ORGANISM: Artificial sequence
<220> FEATURE:
<223> OTHER INFORMATION: the sequence is synthetized.

<400> SEQUENCE: 40
ggagaggggc gtcgacttag cgaggggggca gggc                              34

<210> SEQ ID NO 41
<211> LENGTH: 54
<212> TYPE: DNA
<213> ORGANISM: Artificial sequence
<220> FEATURE:
<223> OTHER INFORMATION: the sequence is synthetized.

<400> SEQUENCE: 41
ccggttctcc gaacgtgtca cgtctcgaga cgtgacacgt tcggagaatt tttg         54

<210> SEQ ID NO 42
<211> LENGTH: 54
<212> TYPE: DNA
<213> ORGANISM: Artificial sequence
<220> FEATURE:
<223> OTHER INFORMATION: the sequence is synthetized.

<400> SEQUENCE: 42
aattcaaaaa ttctccgaac gtgtcacgtc tcgagacgtg acacgttcgg agaa         54

<210> SEQ ID NO 43
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 43
ccgggtgaag ctgagttaat ttatgctcga gtaaattaac tcagcttcac attttttg     59

<210> SEQ ID NO 44
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 44
aattcaaaaa aatgtgaagc tgagttaatt tactcgagca taaattaact cagcttcac    59

<210> SEQ ID NO 45
<211> LENGTH: 59
<212> TYPE: DNA

<213> ORGANISM: Artificial sequence
<220> FEATURE:
<223> OTHER INFORMATION: the sequence is synthetized.

<400> SEQUENCE: 45
ccgggcacag aacttatgtt gttctctcga gaacaacata agttctgtgc ccttttttg    59

<210> SEQ ID NO 46
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 46
aattcaaaaa agggcacaga acttatgttg ttctcgagag aacaacataa gttctgtgc    59

<210> SEQ ID NO 47
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 47
ccggctcaga ttgttgttgt taatgctcga gttaacaaca acaatctgag gttttttg    59

<210> SEQ ID NO 48
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 48
aattcaaaaa aacctcagat tgttgttgtt aactcgagca ttaacaacaa caatctgag    59

<210> SEQ ID NO 49
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 49
ccgggcagct ttaaggagtt cctgcctcga gaggaactcc ttaaagctgc gcttttttg    59

<210> SEQ ID NO 50
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 50
aattcaaaaa agcgcagctt taaggagttc ctctcgaggc aggaactcct taaagctgc    59

<210> SEQ ID NO 51
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 51
ccgggtgtag gcttacctca aataactcga gatttgaggt aagcctacac ttttttttg    59

<210> SEQ ID NO 52
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 52
aattcaaaaa aaagtgtagg cttacctcaa atctcgagtt atttgaggta agcctacac        59

<210> SEQ ID NO 53
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 53
ccggctcaaa taaatggcta acttactcga gagttagcca tttatttgag gttttttg        59

<210> SEQ ID NO 54
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 54
aattcaaaaa aacctcaaat aaatggctaa ctctcgagta agttagccat ttatttgag        59

<210> SEQ ID NO 55
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 55
ccgggatgct tccaatctgg attcactcga gaatccagat tggaagcatc cattttttg        59

<210> SEQ ID NO 56
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 56
aattcaaaaa atggatgctt ccaatctgga ttctcgagtg aatccagatt ggaagcatc        59

<210> SEQ ID NO 57
<211> LENGTH: 59
<212> TYPE: DNA
<213> ORGANISM: Artificial sequence
<220> FEATURE:
<223> OTHER INFORMATION: the sequence is synthetized.

<400> SEQUENCE: 57
ccggcttcca atctggattc aatgactcga gattgaatcc agattggaag cattttttg        59

<210> SEQ ID NO 58
<211> LENGTH: 59
<212> TYPE: DNA
<213> ORGANISM: Artificial sequence
<220> FEATURE:

<223> OTHER INFORMATION: the sequence is synthetized.

<400> SEQUENCE: 58
aattcaaaaa atgcttccaa tctggattca atctcgagtc attgaatcca gattggaag    59

<210> SEQ ID NO 59
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 59
cctttccggg actttcgctt t    21

<210> SEQ ID NO 60
<211> LENGTH: 20
<212> TYPE: DNA
<213> ORGANISM: Artificial sequence
<220> FEATURE:
<223> OTHER INFORMATION: the sequence is synthetized.

<400> SEQUENCE: 60
gcagaatcca ggtggcaaca    20

<210> SEQ ID NO 61
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 61
catgtacgtt gctatccagg c    21

<210> SEQ ID NO 62
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 62
ctccttaatg tcacgcacga t    21

<210> SEQ ID NO 63
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 63
gacttgtggg gtccttctcc t    21

<210> SEQ ID NO 64
<211> LENGTH: 21
<212> TYPE: DNA
<213> ORGANISM: Artificial sequence
<220> FEATURE:
<223> OTHER INFORMATION: the sequence is synthetized.

<400> SEQUENCE: 64
gcagctacag ccatcttcct c    21

```
<210> SEQ ID NO 65
<211> LENGTH: 19
<212> TYPE: DNA
<213> ORGANISM: Artificial sequence
<220> FEATURE:
<223> OTHER INFORMATION: the sequence is synthetized.

<400> SEQUENCE: 65
ggattcaatg aggagactt                                              19

<210> SEQ ID NO 66
<211> LENGTH: 18
<212> TYPE: DNA
<213> ORGANISM: Artificial sequence
<220> FEATURE:
<223> OTHER INFORMATION: the sequence is synthetized.

<400> SEQUENCE: 66
atctgttctg gaggtact                                               18
```